United States Patent
Abbas et al.

(10) Patent No.: US 10,294,205 B2
(45) Date of Patent: May 21, 2019

(54) ALLENAMIDE AS AN ORTHOGONAL HANDLE FOR SELECTIVE MODIFICATION OF CYSTEINE IN PEPTIDES AND PROTEINS

(71) Applicant: Nanyang Technological University, Singapore (SG)

(72) Inventors: Ata Abbas, Singapore (SG); Teck Peng Loh, Singapore (SG); Bengang Xing, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 15/303,670

(22) PCT Filed: Mar. 27, 2015

(86) PCT No.: PCT/SG2015/000100
§ 371 (c)(1),
(2) Date: Oct. 12, 2016

(87) PCT Pub. No.: WO2015/160307
PCT Pub. Date: Oct. 22, 2015

(65) Prior Publication Data
US 2017/0029373 A1    Feb. 2, 2017

Related U.S. Application Data

(60) Provisional application No. 61/980,273, filed on Apr. 16, 2014.

(51) Int. Cl.
| | |
|---|---|
| *C07D 209/14* | (2006.01) |
| *C07D 311/16* | (2006.01) |
| *C07D 403/06* | (2006.01) |
| *C07C 233/09* | (2006.01) |
| *C07C 233/38* | (2006.01) |
| *C07D 493/10* | (2006.01) |
| *C07C 233/07* | (2006.01) |
| *C07C 233/49* | (2006.01) |
| *C07D 209/18* | (2006.01) |
| *C07K 1/13* | (2006.01) |
| *C07K 1/107* | (2006.01) |
| *C07B 59/00* | (2006.01) |
| *A61K 47/54* | (2017.01) |

(52) U.S. Cl.
CPC .......... *C07D 209/14* (2013.01); *A61K 47/54* (2017.08); *C07B 59/002* (2013.01); *C07B 59/004* (2013.01); *C07C 233/07* (2013.01); *C07C 233/09* (2013.01); *C07C 233/38* (2013.01); *C07C 233/49* (2013.01); *C07D 209/18* (2013.01); *C07D 311/16* (2013.01); *C07D 403/06* (2013.01); *C07D 493/10* (2013.01); *C07K 1/1077* (2013.01); *C07K 1/13* (2013.01); *C07B 2200/05* (2013.01); *C07C 2601/14* (2017.05)

(58) Field of Classification Search
CPC .. C07D 209/14; C07D 209/18; C07D 311/16; C07D 403/06; C07D 493/10; C07B 59/002; C07B 59/004; C07C 233/07; C07C 233/09; C07C 233/38; C07C 233/49; A61K 47/54
USPC .......................................................... 514/414
See application file for complete search history.

(56) References Cited

U.S. PATENT DOCUMENTS 6,153,617 A * 11/2000 Bridges ................ C07D 401/04
514/228.2

FOREIGN PATENT DOCUMENTS

| CN | 101508688 A | 8/2009 |
|---|---|---|
| WO | WO-99/06396 | 2/1999 |
| WO | WO-2011/087776 A1 | 7/2011 |
| WO | WO-2012/158122 A1 | 11/2012 |

OTHER PUBLICATIONS

Kushner et al Can. J. Physiol. Pharmacol., 1999, 77, 79-88.*
Haskins Biomedical Mass Spectrometry, 1982, 9(7), 269.*
Gouyette Biomedical and environmental Mass spectrometry, 1988, 15, 243-247.*
Zhao et al Organic Letters, 2008, 10(18), 4037-4040.*
Bibas.*
Himbert et al. CAPLUS abstract of Journal fuer Praktische Chemie/Chemiker-Zeitung, 1996, 338(4), 355-362 (Year: 1996).*
Ringrose et al Biochemica et Biophysica Acta, Nucleic acids and Protein Synthesis, 1973, 299(2), 371-384 (Year: 1973).*
Abbas et al "Allenamides as Orthogonal Handles for Selective Modification of Cysteine in Peptides and Proteins" Angewandte Chemie International Edition vol. 53, pp. 7491-7494, 2014.
Alam et al "Functionalization of Peptides and Proteins by Mukaiyama Aldol Reaction" Journal of the American Chemical Society vol. 132, pp. 9546-9548, 2010.
Ao et al "Biotransformations of Racemic 2,3-Allenenitriles in Biphasic Systems: Synthesis and Transformations of Enantioenriched Axially Chiral 2,3-Allenoic Acids and their Derivatives" The Journal of Organic Chemistry vol. 79, pp. 3103-3110, 2014.
Arkona et al "Propargyl Amides as Irreversible Inhibitors of Cysteine Proteases—A Lesson on the Biological Reactivity of Alkynes" Angewandte Chemie International Edition vol. 52, pp. 8210-8212, 2013.

(Continued)

*Primary Examiner* — Yevgeny Valenrod
(74) *Attorney, Agent, or Firm* — Cesari and McKenna, LLP

(57) ABSTRACT

There is provided a compound of formula I, having the structure: wherein $R^1$ to $R^5$ have the meanings given in the description.

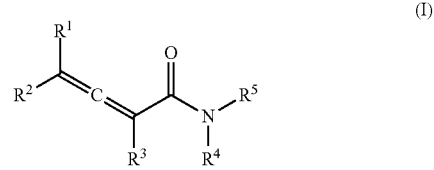

(I)

7 Claims, 13 Drawing Sheets

(56) References Cited

OTHER PUBLICATIONS

Buynak et al "The Preparation of the First α-Vinylidene-β-Lactams" Journal of the Chemical Society Chemical Communications vol. 946, pp. 735-737, 1987.

Chalker et al "Chemical Modification of Proteins at Cysteine: Opportunities in Chemistry and Biology" Chemistry an Asian Journal vol. 4, pp. 630-640, 2009.

Chan et al "Gold-Mediated Selective Cysteine Modification of Peptides Using Allenes" Chemical Communications vol. 49, pp. 1428-1430, 2013.

Chen et al "A Facile Synthesis of β-Allenyl Furanimines via Pd-Catalyzed Cyclization of 2,3-Allenamides with Propargylic Carbonates" Tetrahedron vol. 67, pp. 2332-2337, 2011.

Diehl et al "Intramolekulare Diels-Alder-Reaktion bei Allencarboxaniliden; Inkorporierung des Amid-Stickstoffatoms in Benzo- und Dibenzo-kondensierten Funf-, Sechs- und Siebenringen" Chemische Berichte vol. 119, pp. 2874-2888, 1986.

Ekkebus et al "On Terminal Alkynes that can React with Active-Site Cysteine Nucleophiles in Proteases" Journal of the American Chemical Society vol. 135, pp. 2867-2870, 2013.

Fillion et al "Cerebrovasodilatation Activity and Platelet and Aggregation Inhibition of Allenyl Derivatives" Pharmazie vol. 46, p. 148, 1991.

Fodje et al "Occurrence, Conformational Features and Amino Acid Propensities for the π-Helix" Protein Engineering vol. 15, pp. 353-358, 2002.

Himbert et al "The Thiophene Nucleus as a Diene or a Dienophile in the Intramolecular Diels-Alder Reaction of N-(2-Thienyl)Allene Carboxamides" Journal of the Chemical Society Chemical Communications vol. 9/04709C, pp. 405-406, 1990.

Kostikov "Product Class 1: 1,1-Bis(Heteroatom-Functionalized) Allenes" Science of Synthesis vol. 4.6, pp. 17-36, 2017.

Li et al "CuI-Catalyzed Cross-Coupling of Diazoacetamide with Terminal Alkynes: An Approach to Synthesizing Substituted Dienamides and 3-Butynamides" RSC Advances vol. 3, pp. 21260-21266, 2013.

Lin et al "Allyl Sulfides are Privileged Substrated in Aqueous Cross-Metathesis: Application to Site-Selective Protein Modification" Journal of the American Chemical Society vol. 130, pp. 9642-9643, 2008.

Liu et al "Lipopolysaccharide Neutralizing Peptide-Porphyrin Conjugates for Effective Photoinactivation and Intracellular Imaging of Gram-Negative Bacteria Strains" Bioconjugate Chemistry vol. 23, pp. 1639-1647, 2012.

Pirkle et al "Predictable Chromatographic Separations of Enantiomers: Aryl Allenic Acids and Their Derivatives" Journal of Chromatography A vol. 761, pp. 65-70, 1997.

Reissig et al "Synthesis from Other Allenes" Science of Synthesis vol. 4.6, pp. 301-352, 2017.

Robin et al "Conjugation-Induced Fluorescent Labeling of Proteins and Polymers Using Dithiomaleimides" Journal of the American Chemical Society vol. 135, pp. 2875-2878, 2013.

Roedig et al "Thiol- und Aminaddukte von 3,3-Dichlorallencarboxamiden" Chemische Berichte vol. 116, pp. 1595-1602, 1983.

Schmidt et al "Studies on the Himbert Intramolecular Arene/Allene Diels-Alder Cycloaddition. Mechanistic Studies and Expansion of Scope to All-Carbon Tethers" Journal of the American Chemical Society vol. 135, pp. 7339-7348, 2013.

Shiu et al "Electron-Deficient Alkynes as Cleavable Reagents for the Modification of Cysteine-Containing Peptides in Aqueous Medium" Chemistry a European Journal vol. 15, pp. 3839-3850, 2009.

Smith et al "Protein Modification, Bioconjugation, and Disulfide Bridging Using Bromomaleimides" Journal of the American Chemical Society vol. 132, pp. 1960-1965, 2010.

Sommer et al "Covalent Inhibition of SUMO and Ubiquitin-Specific Cysteine Proteases by an In Situ Thiol-Alkyne Addition" Bioorganic and Medicinal Chemistry vol. 21, pp. 2511-2517, 2013.

Takeuchi et al "Possible Involvement of Radical Intermediates in the Inhibition of Cysteine Proteases by Allenyl Esters and Amides" Bioorganic and Medicinal Chemistry Letters vol. 18, pp. 6202-6205, 2008.

Tedaldi et al "Bromomaleimides: New Reagents for the Selective and Reversible Modification of Cysteine" Chemical Communications vol. 6583, pp. 6583-6585, 2009.

Vondervoort et al "Chromium Catalyzed Oxidation of (Homo-) Allylic and (Homo-)Propargylic Alcohols with Sodium Periodate to Ketones or Carboxylic Acids" Synlett vol. 2, pp. 243-246, 2002.

Zhao et al "Preference of β-Lactam Formation in Cu(L)-Catalyzed Intramolecular Coupling of Amides with Vinyl Bromides" Organic Letters vol. 10, pp. 4037-4040, 2008.

Second Office Action issued in Chinese counterpart application No. 201580020129.1 by the Chinese Patent Office dated May 9, 2018.

Bibas et al "Retro-Ene Reactions in Acylallene Derivatives" Journal of Organic Chemistry vol. 63, pp. 2619-2626, 1998.

Chen et al "Homodimeric Coupling-Cyclization Reaction of 2,3-Allenamides" Tetrahedron vol. 65, pp. 4547-4550, 2009.

Garg et al "Searching for Allosteric Effects Via QSAR. Part II" Bioorganic and Medicinal Chemistry vol. 11, pp. 621-628, 2003.

Himbert et al "Einfluß von Alkylgruppen am Aromaten auf die Intramolekulare Diels-Alder-Reaktion von Allencarbonsaurearylestern und Allencarboxaniliden" Chemische Berichte vol. 121, pp. 431-441, 1988.

Himbert et al "Einfluß von Substituenten in p-, m- und o-Position am Aromaten auf die intramolekulare Diels-Alder Reaktion von Allencarbonsaure-aniliden und -phenylestern" Chemische Berichte vol. 122, pp. 1161-1173, 1989.

Himbert et al "Intramolekulare Diels-Alder-Reaktion bei Allencarboxaniliden; Einbau des 1-Naphthyl-Restes an Stelle monocyclischer Aromatensysteme" Chemische Berichte vol. 119, pp. 3227-3235, 1986.

Koch et al "Ketene-Acetylene [2+2] Cycloadditions: Cyclobutenone and/or Oxete Formation?" Organic and Biomolecular Chemistry vol. 2, pp. 195-199, 2004.

Mo et al "Solvent-Controlled Bifurcated Cascade Process for the Selective Preparation of Dihydrocarbazoles or Dihydropyridoindoles" Chemistry a European Journal vol. 20, pp. 13217-13225, 2014.

Schlindwein et al "Intramolekulare Diels-Alder-Reaktion bei Allencarboxaniliden; Konkurrenz des Anilinkerns mit 'benzylisch-gebundenen' Aromaten und Heteroaromaten" Chemische Berichte vol. 122, pp. 577-584, 1989.

Sletten et al "Bioorthogonal Chemistry: Fishing for Selectivity in a Sea of Functionality" Angewandte Chemie International Edition vol. 48, pp. 6974-6998, 2009.

Trifonov et al "159. Synthesis of 1,2-Five-Ring-Annellated Barrelenes Via the Intramolecular Diels-Alder Reaction of Acetylenic Derivatives" Helvetica Chimica Acta vol. 70, pp. 1732-1736, 1987.

First Office Action issued in Chinese counterpart application No. 201580020129.1 by the Chinese Patent Office dated Sep. 27, 2017.

Extended European Search Report issued in European counterpart application No. 15780447.7 by the European Patent Office dated Mar. 5, 2018.

\* cited by examiner

ALLENAMIDE AS AN ORTHOGONAL HANDLE FOR SELECTIVE MODIFICATION OF CYSTEINE IN PEPTIDES AND PROTEINS

CROSS REFERENCE TO RELATED APPLICATIONS

This application is the National Stage of International Application No. PCT/SG2015/000100, filed on Mar. 27, 2015, which claims the benefit of U.S. Provisional Application No. 61/980,273, filed on Apr. 16, 2014. The contents of both applications are hereby incorporated by reference in their entirety.

BACKGROUND

Among biochemists and chemical biologists, there is a continuous quest for chemical reactions that can potentially be carried out in biological systems. Such chemical reactions may have tremendous applications in various branches of life sciences. However, extremely few reactions can meet the strict requirements of complex biological systems viz., aqueous medium, near neutral pH, ambient temperature, no metal catalysis, no toxic by-product and excellent selectivity for the target functional group.

Proteins and the environment surrounding them are one such complex system, where conducting targeted chemical reactions in a bio-compatible way is still a challenge. Various sites in the protein structure have been targeted for this purpose, among which thiol group of the cysteine residue is one of the most common owing mainly to its high nucleophilicity and relatively low natural abundance (see Chalker, J. M. et al., *Chemistry—An Asian Journal* 4, 630-640, doi:10.1002/asia.200800427 (2009) and Fodje, M. N. et al., *Protein Engineering* 15, 353-358, doi:10.1093/protein/15.5.353 (2002)). However, a versatile reaction for proteins that meets all of the above mentioned requirements still remains elusive.

The most common methodologies, their drawbacks and challenges can be grouped as follows:
(a) classical reagents, such as maleimides, acrylamides and α-halo carbonyl compounds suffer mainly from lack of selectivity, their own stability and toxic by-products;
(b) metal catalyzed reactions that modify the cysteine residue show excellent selectivity (e.g. cross metathesis of allyl sulphides using Ruthenium catalyst by the group of B. G. Davis (Lin, Y. A., et al., *Journal of the American Chemical Society* 130, 9642-9643, doi: 10.1021/ja8026168 (2008)) and thiol-allene coupling using gold catalyst by the group of C. M. Che (On-Yee Chan, A. et al., *Chemical Communications* 49, 1428-1430, doi:10.1039/C2CC38214H (2013)). However, the necessity to use metal complexes renders these reactions unfit for many biological applications;
(c) the use of electron deficient alkynes (Shiu, H.-Y. et al., *Chemistry—A European Journal* 15, 3839-3850, doi: 10.1002/chem.200800669 (2009)), or bromomaleimides (Tedaldi, L. M., et al., *Chemical Communications*, 6583-6585, doi:10.1039/B915136B (2009) and Smith, M. E. B. et al., *Journal of the American Chemical Society* 132, 1960-1965, doi:10.1021/ja908610s (2010)) and dithiomaleimide derivatives (Robin, M. P. et al., *Journal of the American Chemical Society* 135, 2875-2878, doi:10.1021/ja3105494 (2013)). These reactions show excellent selectivity and have the advantage of being reversible under the presence of excess thiol. However, the reversibility poses a limitation when an in-vivo application is required because of the presence of a large excess of glutathione in the intracellular environment.

Two groups (Ovaa and Mootz) have recently demonstrated simultaneously and independently that terminal alkynes (in modified ubiquitin) can be used to inhibit cysteine proteases irreversibly through in-situ thiol-alkyne coupling (Ekkebus, R. et al., *Journal of the American Chemical Society* 135, 2867-2870, doi:10.1021/ja309802n (2013) and Sommer, S., et al., *Bioorganic & Medicinal Chemistry* 21, 2511-2517, (2013)), which is quite impressive and surprising as alkynes have largely been considered inert under biological conditions. However, this coupling is not versatile as activation of an alkyne by a positively charged protein pocket (an oxoanion hole) has been proposed to be necessary for this unexpected reactivity (Arkona, C. et al., *Angewandte Chemie International Edition*, doi:10.1002/anie.201303544 (2013)).

With the long term goal to understand and regulate protein functions through their chemical modification, our group has previously reported modification of the N-terminus of peptides and proteins using Mukaiyama aldol condensation (Alam, J., et al., *Journal of the American Chemical Society* 132, 9546-9548, doi:10.1021/ja102733a (2010)).

However, there remains an urgent need to find a promising orthogonal handle and related labelling strategies that can selectively and irreversibly bind with cysteine, without the requirement for special local conditions (e.g. a positively charged protein pocket).

BRIEF DESCRIPTION OF DRAWINGS

FIG. 4 is an MS spectrum showing MS/MS of the peptide CGKSRF modified with allenamide 1a.

FIG. 5 is an MS spectrum showing MS/MS of the peptide KSCGRF modified with allenamide 1a.

FIG. 6 is an MS spectrum showing MS/MS of peptide YDSQCFHRW modified with allenamide 1a.

FIG. 10 illustrates the modification of Bovine Insulin with allenamide 1a.

FIG. 11 is an MS spectrum showing MS/MS of chain A of bovine insulin modified with allenamide 1a.

FIG. 12 is an MS spectrum showing MS/MS of chain B of bovine insulin modified with allenamide 1a.

FIG. 13 depicts the MS/MS result for the modification of Bovine Serum Albumin with allenamide 1a.

DESCRIPTION

Figure 1:
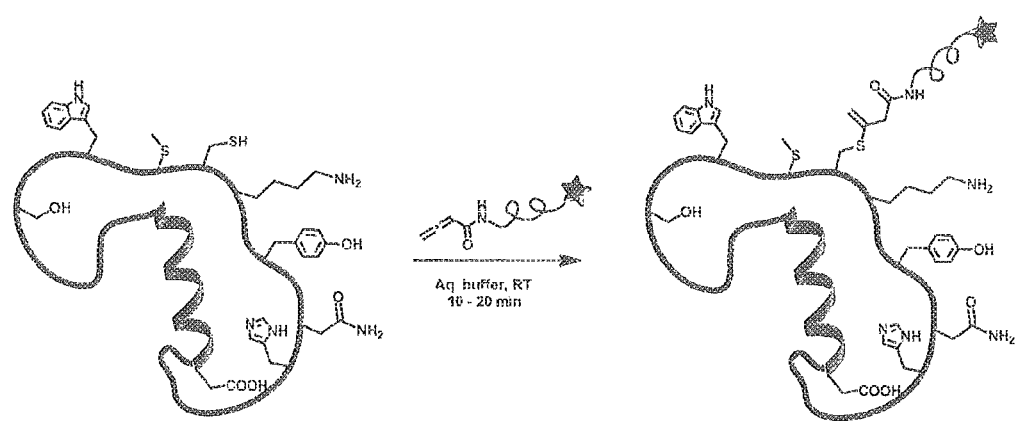
FIG. 1 is an illustration showing selective modification of cysteine residue in proteins.

In a first aspect of the invention, there is provided a compound of formula I,

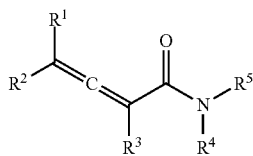

I wherein:

R$^1$, R$^2$ and R$^3$ independently represent H, halo, CN, C$_{1-12}$ alkyl, C$_{2-12}$ alkenyl, C$_{2-12}$ alkynyl (which latter three groups are unsubstituted or substituted by one or more substituents selected from halo, nitro, CN, C$_{1-6}$ alkyl, C$_{2-6}$ alkenyl, C$_{2-6}$ alkynyl (which latter three groups are unsubstituted or substituted by one or more substituents selected from OH, =O, halo, C$_{1-4}$ alkyl and C$_{1-4}$ alkoxy), OR$^{6a}$, S(O)$_q$R$^{6b}$, S(O)$_2$NR$^{6c}$R$^{6d}$, NR$^{6e}$S(O)$_2$R$^{6f}$, NR$^{6g}$R$^{6h}$, aryl and Het$^1$), Cy$^1$ (which Cy$^1$ group is optionally substituted by one or more substituents selected from halo, nitro, CN, C$_{1-6}$ alkyl, C$_{2-6}$ alkenyl, C$_{2-6}$alkynyl (which latter three groups are unsubstituted or substituted by one or more substituents selected from OH, =O, halo, C$_{1-4}$ alkyl and C$_{1-4}$ alkoxy), OR$^{7a}$, S(O)$_q$R$^{7b}$, S(O)$_2$NR$^{7c}$R$^{7d}$, NR$^{7e}$S(O)$_2$R$^{7f}$, NR$^{7g}$R$^{7h}$, aryl and Het$^2$), Het$^a$ (which Het$^a$ group is unsubstituted or substituted by one or more substituents selected from halo, nitro, CN, C$_{1-6}$ alkyl, C$_{2-6}$ alkenyl, C$_{2-6}$alkynyl (which latter three groups are unsubstituted or substituted by one or more substituents selected from OH, =O, halo, C$_{1-4}$ alkyl and C$_{1-4}$ alkoxy), OR$^{8a}$, S(O)$_q$R$^{8b}$, S(O)$_2$NR$^{8c}$R$^{8d}$, NR$^{8e}$S(O)$_2$R$^{8f}$, NR$^{8g}$R$^{8h}$, aryl and Het$^3$), OR$^{9a}$, S(O)$_q$R$^{9b}$, S(O)$_2$NR$^{9c}$R$^{9d}$, NR$^{9e}$S(O)$_2$R$^{9f}$ and NR$^{9g}$R$^{9h}$;

R$^4$ and R$^5$ independently represent H, C$_{1-12}$ alkyl, C$_{2-12}$ alkenyl, C$_{2-12}$ alkynyl (which latter three groups are unsubstituted or substituted by one or more substituents selected from halo, nitro, CN, C$_{1-6}$ alkyl, C$_{2-6}$ alkenyl, C$_{2-6}$ alkynyl (which latter three groups are unsubstituted or substituted by one or more substituents selected from OH, =O, halo, C$_{1-4}$ alkyl and C$_{1-4}$ alkoxy), =O, OR$^{10a}$, S(O)$_q$R$^{10b}$, S(O)$_2$NR$^{10c}$R$^{10d}$, NR$^{10e}$S(O)$_2$R$^{10f}$, NR$^{10g}$R$^{10h}$, aryl and Het$^4$ or a fluorescent group), aryl, Cy$^2$ (which latter two groups are unsubstituted or substituted by one or more substituents selected from halo, nitro, CN, C$_{1-6}$ alkyl, C$_{2-6}$ alkenyl, C$_{2-6}$alkynyl (which latter three groups are unsubstituted or substituted by one or more substituents selected from OH, =O, halo, C$_{1-4}$ alkyl and C$_{1-4}$alkoxy), OR$^{11a}$, S(O)$_q$R$^{11b}$, S(O)$_2$NR$^{11c}$R$^{11d}$, NR$^{11e}$S(O)$_2$R$^{11f}$, NR$^{11g}$R$^{11h}$, aryl and Het$^5$), Het$^b$ (which Het$^b$ group is unsubstituted or substituted by one or more substituents selected from halo, nitro, CN, C$_{1-6}$ alkyl, C$_{2-6}$ alkenyl, C$_{2-6}$alkynyl (which latter three groups are unsubstituted or substituted by one or more substituents selected from OH, =O, halo, C$_{1-4}$ alkyl and C$_{1-4}$alkoxy), OR$^{12a}$, S(O)$_q$R$^{12b}$, S(O)$_2$NR$^{12c}$R$^{12d}$, NR$^{12e}$S(O)$_2$R$^{12f}$, NR$^{12g}$R$^{12h}$, aryl and Het$^6$), OR$^{13a}$ and S(O)$_q$R$^{13b}$, or R$^4$ and R$^5$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, C$_{1-6}$ alkyl, C$_{2-6}$ alkenyl, C$_{2-6}$ alkynyl (which latter three groups are optionally substituted by one or more substituents selected from OH, =O, halo, C$_{1-4}$ alkyl and C$_{1-4}$ alkoxy);

Het$^1$ to Het$^6$ independently represent 4- to 14-membered heterocyclic groups containing one or more heteroatoms selected from O, S and N, which heterocyclic groups may comprise one, two or three rings and may be substituted by one or more substituents selected from halo, C$_{1-6}$ alkyl, C$_{2-6}$alkenyl (which latter two groups are optionally substituted by one or more substituents selected from halo, and Het$^7$), and OR$^{14}$;

Het$^7$ independently represents a 4- to 14-membered heterocyclic group containing one or more heteroatoms selected from O, S and N, which heterocyclic groups may comprise one, two or three rings and may be substituted by one or more substituents selected from halo, C$_{1-6}$ alkyl, C$_{2-6}$alkenyl (which latter two groups are optionally substituted by one or more substituents selected from halo), S(O)$_q$R$^{15a}$ and OR$^{15b}$;

Cy$^1$ and Cy$^2$ represent, independently at each occurrence, a 3- to 6-membered aromatic, fully saturated or partially unsaturated carbocyclic ring;

R$^{6a}$ to R$^{6h}$, R$^{7a}$ to R$^{7h}$, R$^{8a}$ to R$^{8h}$, R$^{9a}$ to R$^{9h}$, R$^{10a}$ to R$^{10h}$, R$^{11a}$ to R$^{11h}$, R$^{12a}$ to R$^{12h}$, R$^{13a}$ to R$^{13h}$, independently represent, at each occurrence, H, C$_{1-10}$ alkyl, C$_{2-10}$ alkenyl, C$_{2-10}$ alkynyl (which latter three groups are unsubstituted or substituted by one or more substituents selected from halo, nitro, CN, C$_{1-6}$ alkyl, C$_{2-6}$ alkenyl, C$_{2-6}$ alkynyl, C$_{3-6}$ cycloalkyl (which latter four groups are unsubstituted or substituted by one or more substituents selected from OH, =O, halo, C$_{1-4}$ alkyl and C$_{1-4}$ alkoxy), OR$^{16a}$, S(O)$_q$R$^{16b}$, S(O)$_2$NR$^{16c}$R$^{16d}$, NR$^{16e}$S(O)$_2$R$^{16f}$, NR$^{16g}$R$^{16h}$, aryl and Het$^8$), C$_{3-10}$ cycloalkyl, C$_{4-10}$ cycloalkenyl (which latter two groups are optionally substituted by one or more substituents selected from halo, OH, =O, C$_{1-6}$ alkyl and C$_{1-6}$ alkoxy) or Het$^c$, or R$^{6-12c}$ and R$^{6-12d}$, and R$^{6-12g}$ and R$^{6-12h}$ may represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, C$_{1-6}$ alkyl, C$_{2-6}$ alkenyl, C$_{2-6}$ alkynyl (which latter three groups are optionally substituted by one or more substituents selected from OH, =O, halo, C$_{1-4}$ alkyl and C$_{1-4}$ alkoxy); alternatively R$^{10g}$ represents H and R$^{10h}$ represents C(S)NR$^{17a}$R$^{17b}$;

Het$^a$ to Het$^c$ independently represent 4- to 14-membered heterocyclic groups containing one or more heteroatoms selected from O, S and N;

Het$^8$ independently represents a 4- to 14-membered heterocyclic group containing one or more heteroatoms selected from O, S and N, which heterocyclic group may comprise one, two or three rings and may be substituted by one or more substituents selected from halo, C$_{1-6}$ alkyl, which latter group is optionally substituted by one or more substituents selected from halo, —OR$^{18a}$ and —NR$^{18b}$R$^{18c}$;

R$^{14}$, R$^{15a}$, R$^{15b}$, R$^{16a}$ to R$^{16h}$ and R$^{18a}$ to R$^{18c}$ independently represent at each occurrence, H, C$_{1-4}$ alkyl, C$_{2-4}$ alkenyl, C$_{2-4}$ alkynyl which latter three groups are optionally substituted by one or more substituents selected from halo, nitro, CN, C$_{1-4}$ alkyl, C$_{2-4}$ alkenyl, C$_{2-4}$ alkynyl (which latter three groups are optionally substituted by one or more substituents selected from OH, =O, halo, C$_{1-4}$ alkyl and C$_{1-4}$ alkoxy), C$_{3-6}$ cycloalkyl, or C$_{4-6}$ cycloalkenyl (which latter two groups are optionally substituted by one or more substituents selected from halo, OH, =O, C$_{1-4}$ alkyl and C$_{1-4}$ alkoxy), R$^{17a}$ represents H;

R$^{17b}$ represents Het$^9$ or a fluorescent group;

Het$^9$ represents a 4- to 22-membered heterocyclic group containing one or more heteroatoms selected from O, S and N, which heterocyclic group may comprise one to five rings and may be substituted by one or more substituents selected from halo, $C_{1-6}$ alkyl (which latter group is optionally substituted by one or more substituents selected from halo, $OR^{19a}$ and $NR^{19b}R^{19c}$), =O, $OR^{20a}$ and $NR^{20b}R^{20c}$;

$R^{19a}$ to $R^{19c}$ and $R^{20a}$ to $R^{20c}$ independently represent at each occurrence, H, $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, =O, halo, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from halo, OH, =O, $C_{1-4}$ alkyl and $C_{1-4}$ alkoxy);

q, at each occurrence, represents 0, 1 or 2, or a pharmaceutically acceptable salt, solvate or a pharmaceutically functional derivative thereof, provided that the compound of formula I is not 4,4-dichloro-N-(propan-2-yl)buta-2,3-dienamide, N-tert-butyl-4,4-dichlorobuta-2,3-dienamide or 4,4-dichloro-N-(4-methylphenyl)buta-2,3-dienamide.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

"Pharmaceutically functional derivatives" of compounds of formula I as defined herein includes ester derivatives and/or derivatives that have, or provide for, the same biological function and/or activity as any relevant compound of the invention. Thus, for the purposes of this invention, the term also includes prodrugs of compounds of formula I.

The term "prodrug" of a relevant compound of formula I includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

In a second aspect of the invention, there is provided a use of a compound of formula I as an irreversible binder to a free thiol group.

In certain embodiments of the invention:
(i) the free thiol group is part of a peptide or a protein;
(ii) the use is in vitro or in vivo;
(iii) the use is in aqueous media or in physiological conditions, or equivalents thereof.

In a third aspect of the invention, there is provided a compound of formula I for use in medicine.

The compound for use mentioned in the above-mentioned aspect of the invention may be utilised in a method of medical treatment. Thus, according to further aspects of the invention, there is provided:
(i) the use of a compound formula I for the manufacture of a medicament for the treatment of a condition or disorder ameliorated by inhibition of a cysteine protease;
(ii) a method of treatment of a disorder or condition ameliorated by antagonising a cysteine protease, which method comprises the administration of an effective amount of a compound of formula I to a patient in need of such treatment; and
(iii) a compound of formula I for use in the treatment of a condition or disorder ameliorated by inhibition of a cysteine protease The term "disorder or condition ameliorated by the inhibition of a cysteine protease" will be understood by those skilled in the art to include: parasitic diseases (periodontitis; malaria; chagasheart disease); neurological disorders (Alzheimer's disease; transmissible spongiform encephalopathies), cancer, inflammatory/immune system diseases (e.g. multiple sclerosis); atherosclerosis; emphysema; muscular dystrophy; osteoporosis; and rheumatoid arthritis.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

The term "halo", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Heterocyclic ($Het^1$ to $Het^9$ and $Het^a$ to $Het^c$) groups may be fully saturated, partly unsaturated, wholly aromatic or partly aromatic in character. Values of $Het^1$ to $Het^9$ and $Het^a$ to $Het^c$ groups that may be mentioned include acridinyl, 1-azabicyclo[2.2.2]octanyl, azetidinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[b]furanyl, 1,3-dihydrobenzo[c]furanyl, 1,3-dihydro-2,1-benzisoxazolyl, 2,3-dihydropyrrolo[2,3-6]pyridinyl, dioxanyl, furanyl, furazanyl, hexahydropyrimidinyl, hydantoinyl, imidazolyl, imidazo[1, 2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiaziolyl, isothiochromanyl, isoxazolidinyl, isoxazolyl, maleimido, morpholinyl, naphtho[1, 2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, oxetanyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), tetrazolyl, thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like.

Substituents on heterocyclic ($Het^1$ to $Het^9$ and $Het^a$ to $Het^c$) groups may, where appropriate, be located on any atom in the ring system including a heteroatom. The point of attachment of heterocyclic ($Het^1$ to $Het^9$ and $Het^a$ to $Het^c$)

groups may be via any atom in the ring system including (where appropriate) a heteroatom (such as a nitrogen atom), or an atom on any fused carbocyclic ring that may be present as part of the ring system. Heterocyclic ($Het^1$ to $Het^9$ and $Het^a$ to $Het^c$) groups may also be in the N- or S-oxidised form.

For the avoidance of doubt, in cases in which the identity of two or more substituents in a compound of formula I may be the same, the actual identities of the respective substituents are not in any way interdependent. For the avoidance of doubt, when a term such as "$R^{19a}$ to $R^{19c}$" is employed herein, this will be understood by the skilled person to mean any (i.e. some or all, as applicable) of $R^{19a}$, $R^{19b}$ and $R^{19c}$ inclusively.

Embodiments of the invention that may be mentioned include those that relate to compounds of formula I in which:

(a) $R^1$ to $R^3$ independently represent H, halo, CN, $C_{1-6}$ alkyl (which latter group are unsubstituted or substituted by one or more substituents selected from halo, nitro, CN, $C_{1-4}$ alkyl, $C_{2-3}$ alkenyl, $C_{2-3}$ alkynyl (which latter three groups are unsubstituted or substituted by one or more substituents selected from OH, =O, halo, $C_{1-4}$ alkyl and $C_{1-4}$ alkoxy), $OR^{6a}$ and $NR^{6g}R^{6h}$), $Cy^1$ (which $Cy^1$ group is optionally substituted by one or more substituents selected from halo, nitro, CN, $C_{1-4}$ alkyl, $C_{2-3}$ alkenyl, $C_{2-3}$ alkynyl (which latter three groups are unsubstituted or substituted by one or more substituents selected from OH, =O, halo, $C_{1-4}$ alkyl and $C_{1-4}$ alkoxy), $OR^{7a}$ and $NR^{7g}R^{7h}$), $Het^a$ (which $Het^a$ group is unsubstituted or substituted by one or more substituents selected from halo, nitro, CN, $C_{1-4}$ alkyl, $C_{2-3}$ alkenyl, $C_{2-3}$ alkynyl (which latter three groups are unsubstituted or substituted by one or more substituents selected from OH, =O, halo, $C_{1-4}$ alkyl and $C_{1-4}$ alkoxy), $OR^{8a}$ and $NR^{8g}R^{8h}$), $OR^{9a}$ and $NR^{9g}R^{9h}$ (e.g. $R^1$ to $R^3$ independently represent H);

(b) $R^4$ and $R^5$ independently represent H, $C_{1-6}$ alkyl, $C_{2-6}$ alkenyl, $C_{2-6}$ alkynyl (which latter three groups are unsubstituted or substituted by one or more substituents selected from halo, nitro, CN, $C_{1-4}$ alkyl, $C_{2-3}$ alkenyl, $C_{2-3}$ alkynyl (which latter three groups are unsubstituted or substituted by one or more substituents selected from OH, =O, halo, $C_{1-4}$ alkyl and $C_{1-4}$ alkoxy), =O, $OR^{10a}$, $S(O)_qR^{10b}$, $NR^{10g}R^{10h}$, aryl and $Het^4$ or a fluorescent group), aryl, $Cy^2$ (which latter two groups are unsubstituted or substituted by one or more substituents selected from halo, nitro, CN, $C_{1-4}$ alkyl, $C_{2-3}$ alkenyl, $C_{2-3}$alkynyl (which latter three groups are unsubstituted or substituted by one or more substituents selected from OH, =O, halo, $C_{1-4}$ alkyl and $C_{1-4}$alkoxy), $OR^{11a}$ and $NR^{11g}R^{11h}$), $Het^b$ (which $Het^b$ group is unsubstituted or substituted by one or more substituents selected from halo, nitro, CN, $C_{1-4}$ alkyl, $C_{2-3}$ alkenyl, $C_{2-3}$ alkynyl (which latter three groups are unsubstituted or substituted by one or more substituents selected from OH, =O, halo, $C_{1-4}$ alkyl and $C_{1-4}$alkoxy), $OR^{12a}$ and $NR^{12g}R^{12h}$), $OR^{13a}$ and $S(O)_qR^{13b}$, or $R^4$ and $R^5$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$alkoxy). For example, $R^4$ represents H and $R^5$ represents H, $C_{1-6}$ alkyl (which latter group is unsubstituted or substituted by one or more substituents selected from halo, nitro, CN, =O, $OR^{10a}$ and $Het^4$ or a fluorescent group), aryl, $Cy^2$ (which latter two groups are unsubstituted or substituted by one or more substituents selected from halo, nitro, CN, $C_{1-4}$alkyl (which latter group is unsubstituted or substituted by one or more substituents selected from OH, =O, halo, $C_{1-4}$ alkyl and $C_{1-4}$ alkoxy), $OR^{10a}$ and $NR^{11h}R^{11h}$), $Het^b$ (which $Het^b$ group is unsubstituted or substituted by one or more substituents selected from halo, nitro, CN, $C_{1-4}$ alkyl, $OR^{12a}$ and $NR^{12g}R^{12h}$) and $OR^{13a}$;

(c) $Het^1$ to $Het^6$ independently represent 6- to 10-membered heterocyclic groups containing one or more heteroatoms selected from O, S and N, which heterocyclic groups may comprise one, two or three rings and may be substituted by one or more substituents selected from halo, $C_{3-5}$ alkyl, $C_{3-5}$ alkenyl (which latter two groups are optionally substituted by one or more substituents selected from halo, and $Het^7$), and $OR^{14}$. For example, $Het^4$ represents a 6- to 10-membered heterocyclic group containing one or more heteroatoms selected from O, S and N, which heterocyclic group may comprise one or two rings and may be substituted by one or more substituents selected from halo, $C_{3-5}$alkenyl (which latter group is substituted by a $Het^7$ substituent), and $OR^{14}$;

(d) $Het^7$ independently represents a 6- to 10-membered heterocyclic group containing one or more heteroatoms selected from O, S and N, which heterocyclic groups may comprise one or two rings and may be substituted by one or more substituents selected from halo, $C_{1-6}$ alkyl, $S(O)_qR^{15a}$ and $OR^{15b}$;

(e) $Cy^1$ and $Cy^2$ represent, independently at each occurrence, a 5- to 6-membered aromatic, fully saturated or partially unsaturated carbocyclic ring;

(f) $R^{6a}$ to $R^{6h}$, $R^{7a}$ to $R^{7h}$, $R^{8a}$ to $R^{8h}$, $R^{9a}$ to $R^{9h}$, $R^{10a}$ to $R^{10h}$, $R^{11a}$ to $R^{11h}$, $R^{12a}$ to $R^{12h}$, $R^{13a}$ to $R^{13h}$, independently represent, at each occurrence, H, $C_{1-4}$ alkyl, $C_{2-3}$ alkenyl, $C_{2-3}$ alkynyl (which latter three groups are unsubstituted or substituted by one or more substituents selected from halo, nitro, CN, $C_{1-4}$ alkyl (which latter group is unsubstituted or substituted by one or more substituents selected from OH, =O, halo, $C_{1-4}$ alkyl and $C_{1-4}$ alkoxy), $OR^{16a}$, $NR^{16g}R^{16h}$, aryl and $Het^8$), or $R^{10g}$ represents H and $R^{10h}$ represents $C(S)NR^{17a}R^{17b}$;

(g) $Het^a$ to $Het^c$ independently represent 6- to 10-membered heterocyclic groups containing one or more heteroatoms selected from O, S and N; and/or $Het^8$ independently represents a 6- to 10-membered heterocyclic group containing one or more heteroatoms selected from O, S and N, which heterocyclic group may comprise one, or two rings and may be substituted by one or more substituents selected from halo, $C_{1-6}$ alkyl, which latter group is optionally substituted by one or more substituents selected from halo, $OR^{18a}$ and $NR^{18b}R^{18c}$;

(h) $R^{14}$, $R^{15a}$, $R^{15b}$, $R^{16a}$ to $R^{16h}$ and $R^{18a}$ to $R^{18c}$ independently represent at each occurrence, H, $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, =O, halo, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from halo, OH, =O, $C_{1-4}$ alkyl and $C_{1-4}$ alkoxy);

(i) $Het^9$ represents a 10- to 22-membered heterocyclic group containing one or more heteroatoms selected from O, S and N, which heterocyclic group may comprise three, four or five rings and may be substituted by one or more substituents selected from halo, $C_{1-6}$ alkyl, =O, $OR^{20a}$, $NR^{20b}R^{20c}$.

In yet further embodiments of the invention, the compound of formula I may be selected from the group consisting of:

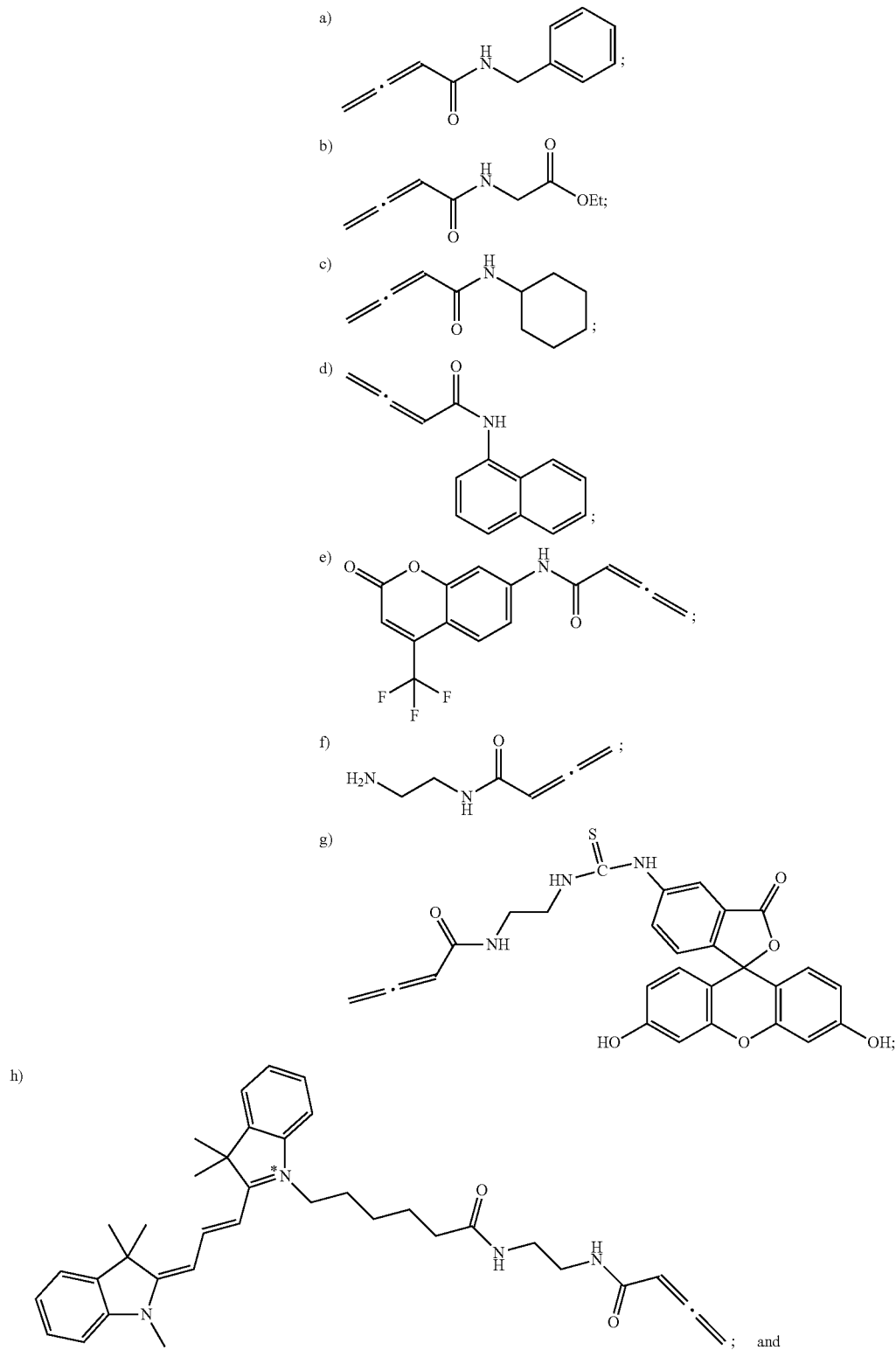

i)
-continued

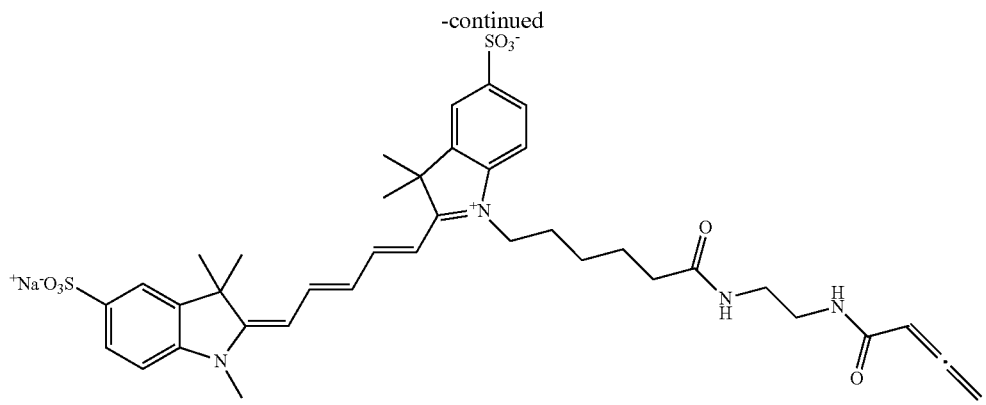

or a pharmaceutically acceptable salt or solvate, or a pharmaceutically functional derivative thereof.

Further embodiments of the invention that may be mentioned include those in which the compound of formula I is isotopically labelled. However, other, particular embodiments of the invention that may be mentioned include those in which the compound of formula I is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I. Thus, the term "isotopically labelled" includes references to compounds of formula I that are isotopically enriched at one or more positions in the compound.

The isotopic labelling or enrichment of the compound of formula I may be with a radioactive or non-radioactive isotope of any of hydrogen, carbon, nitrogen, oxygen, sulfur, fluorine, chlorine, bromine and/or iodine. Particular isotopes that may be mentioned in this respect include $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{37}$Cl, $^{77}$Br, $^{82}$Br and $^{125}$I).

When the compound of formula I is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

Compounds of formula I may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula I in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

As mentioned above, compounds of formula I may bind selectively to free thiol groups, and may therefore have utility as diagnostic agents for determining the presence and/or location (either in vivo or in vitro) of free thiol groups (i.e. in a cysteine protease).

Thus, according to a further aspect of the invention there is provided a method (e.g. an in vivo or, particularly, an ex vivo method) of determining the presence and/or location of free thiol groups in a tissue sample, said method comprising contacting the tissue sample with a compound of formula I and then detecting by a visualising method the location of the compound of formula I in the sample.

Visualising methods that may be mentioned include spectroscopic detection methods (e.g. fluorescence detection, magnetic resonance imaging, etc.) or, when the compound of formula I is isotopically labelled or enriched with a radioisotope (such as $^3$H, $^{11}$C, $^{35}$S, $^{18}$F, or $^{125}$I), radioactivity detection methods (e.g. alpha-, beta- or gamma-detection by standard autoradiography, phosphor or scintillation methods known to those skilled in the art, or positron emission tomography (which latter method may be employed, for example, when the compound of formula I is isotopically labelled or enriched with $^{11}$C, or, particularly, $^{18}$F)).

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

Compounds of formula I may be prepared in accordance with techniques that are well known to those skilled in the art, for example as described hereinafter.

Compounds of the invention may be isolated from their reaction mixtures using conventional techniques (e.g. recrystallisation, column chromatography, preparative HPLC, etc.).

In the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

As used herein, the term "functional groups" means, in the case of unprotected functional groups, hydroxy-, thiolo-, aminofunction, carboxylic acid and, in the case of protected functional groups, lower alkoxy, N-, O-, S-acetyl, carboxylic acid ester.

In yet a further aspect of the invention, there is provided a use of a compound of formula I as an imaging or diagnostic agent. For example, the compound of formula I may be isotopically labelled and/or is selected from the group consisting of:

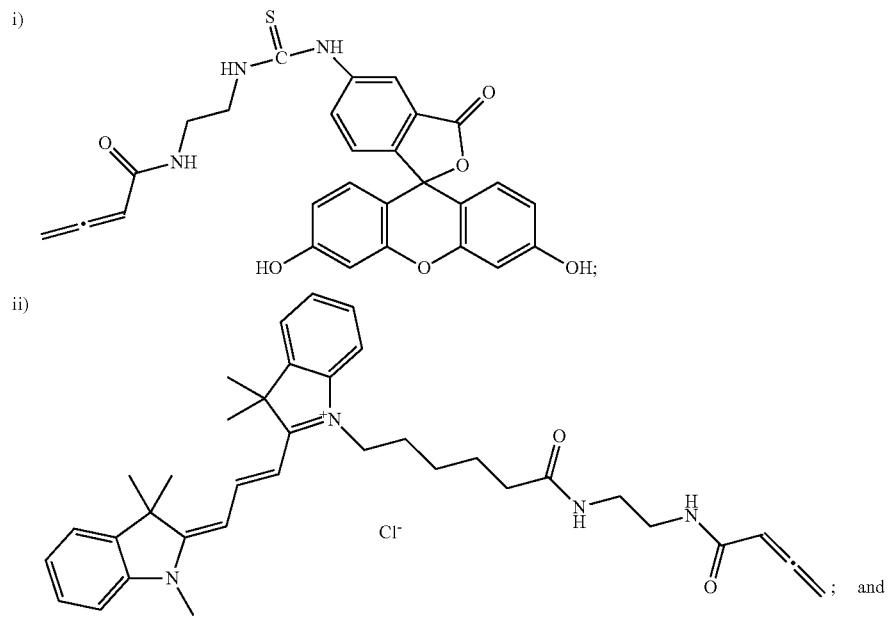

iii)

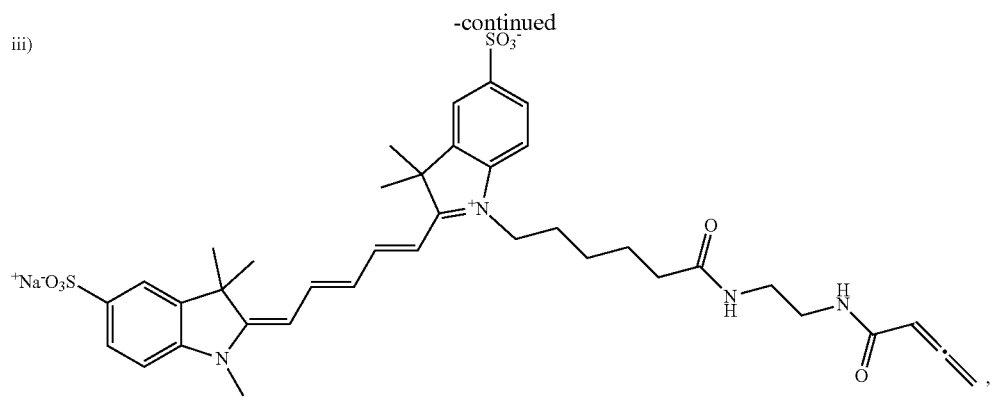

or a pharmaceutically acceptable salt or solvate, or a pharmaceutically functional derivative thereof.

In a further aspect of the invention, there is further provided a compound comprising an allenamide covalently attached, optionally by way of a linker, to a biomolecule or a material having diagnostic or imaging properties, or a pharmaceutically acceptable salt or solvate, or a pharmaceutically functional derivative thereof. In a further related aspect of the invention, the compound described herein may be used as a diagnostic or imaging agent.

EXAMPLES

General

All chemicals were purchased from commercial suppliers (Sigma Aldrich, Merck, Alfa Aesar and TCI) and were used without further purification. Amino acids for peptide synthesis were purchased from GL Biochem. NMR spectra were recorded using either a Bruker 300 or 400 MHz spectrometer. Mass spectra were recorded on a Thermo LCQ FLEET instrument. HPLC purification of compounds 14 and 15 was performed on a reverse phase Shimadzu HPLC system using an Alltima C-18 (250×10 mm) column at a flow rate of 3 mL/min. Fluorescence emission spectra were recorded on a Typhoon TRIO Variable Mode Imager. LC-MS/MS spectra were recorded on Dionex UHPLC and LTQ orbitrap instrument having a Dionexpepmap C-18 column. The data generated after MS/MS of BSA protein was analysed by gpm software.

Preparations

Preparation 1: Synthesis of 3-butynoic acid

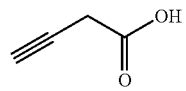

3-butynoic acid was prepared from the oxidation of 3-butyn-1-ol and following the reported procedure (Schmieder-van de Vondervoort, L. et al., P. L. *Synlett* 2002, 2002, 0243). Water (45 mL) was added to a 150 mL single neck RBF fitted with a magnetic, stirrer bar. 65% $HNO_3$ (0.17 mL, 5 mol %, 2.5 mmol), $Na_2Cr_2O_7$ (0.15 g, 1 mol %, 0.5 mmol) and $NaIO_4$ (23.53 g, 2.2 eq., 110 mmol) were subsequently added to the RBF and the mixture was stirred vigorously on an ice bath for 15 min. 3.78 mL of 3-butyn-1-ol (1 eq., 50 mmol) dissolved in 45 mL of chilled water was added to this mixture slowly and the reaction mixture was left for 18-24 hrs (ice bath was not removed to let the ice melt and temperature of reaction mixture rise slowly to rt). After this time, the product was extracted in diethyl ether (80 mL×6). All of the fractions were combined and dried over anhydrous magnesium sulphate. The solvent was removed using a rotary evaporator to give an orange/yellowish viscous liquid. Subsequent addition of dichloromethane and removal of solvent on a rotary evaporator (under vacuum) 4-5 times gave 3.20 g of an off white/yellowish solid (38 mmol, yield 76%).

$^1$H NMR (400 MHz, $CDCl_3$) δ 3.38 (d, 2H, J=2.7 Hz), 2.25 (t, 1H, J=2.7 Hz); $^{13}$C NMR (400 MHz, $CDCl_3$) δ 173.8, 74.8, 72.4, 25.6

Preparation 2: Synthesis of tert-butyl (2-aminoethyl)carbamate (N-Boc-Ethylenediamine)

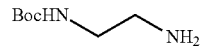

The title compound was synthesized using the procedure reported in Liu, F. et al., *Bioconjugate Chemistry* 2012, 23, 1639.

$^1$H NMR (400 MHz, CDCl3) δ 5.35 (s, 1H), 3.15 (t, 2H, J=5.7 Hz), 2.79 (t, 2H, J=5.9 Hz), 1.45 (s, 9H); $^{13}$C NMR (400 MHz, CDCl3) δ 156.1, 78.7, 53.2, 43.2, 41.6, 28.2

Synthesis of Compounds and Peptides

General Procedure for the Synthesis of Allenamides

3-Butynoic acid was stirred with 1.5 equivalents of Mukaiyama reagent (2-chloro-1-methyl pyridinium iodide) in dry dichloromethane at room temperature for one hour without any base. After one hour, a solution of the desired amine (1.1 eq.) and triethylamine (1.5 eq.) in dry dichloromethane was added to the 3-butynoic acid mixture dropwise. A slight exotherm was observed during this step, after which the reaction mixture was stirred for another half an hour. After this time, the dichloromethane was removed using a rotary evaporator and ethyl acetate was added to the solid residue which was then transferred to a separatory funnel. The organic layer was washed 2 times with water and dried on anhydrous sodium sulphate. Solvent was evaporated to provide the crude product which was purified by column chromatography. Yields were found to be sensitive to the amount of triethylamine used with excess TEA giving poorer yields.

Synthesis of N-benzylbuta-2,3-dienamide (1a)

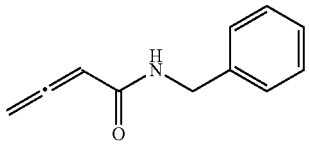

3-Butynoic acid (preparation 1, 0.23 g, 1 eq., 2.76 mmol) and 1.05 g of 2-chloro-1-methyl pyridinium iodide (1.5 eq., 4.13 mmol) were charged in a 25 mL two neck oven dried RBF fitted with a magnetic stirrer bar. 10 mL dry dichloromethane was added to it and the mixture was stirred under nitrogen for 1 hr. A solution of 0.33 mL of benzylamine (1.1 eq., 3.03 mmol) and 0.6 mL triethylamine (1.5 eq., 4.55 mmol) in 5 mL dry dichloromethane was added to it drop wise after which the reaction mixture was stirred for another half an hour.

After the work up as described above, product was purified by flash column chromatography (20-30% EA in hexane) to get 0.3212 g of 1 (1.86 mmol; 67% yield).

$^1$H NMR (400 MHz, CDCl$_3$) δ 7.34-7.25 (m, 5H), 6.31 (s, 1H), 5.67 (t, 1H, J=6.6 Hz), 5.19 (d, 2H, J=6.7 Hz), 4.46 (d, 2H, J=5.9 Hz); $^{13}$C NMR (400 MHz, CDCl$_3$) δ 212.0, 164.5, 138.2, 128.7, 127.8, 127.5, 90.8, 80.6, 43.7; ESI-MS calculated for C$_{11}$H$_{11}$NO [M+H]$^+$ m/z 174.09. found 174.02.

Synthesis of ethyl 2-(buta-2,3-dienamido)acetate (1b)

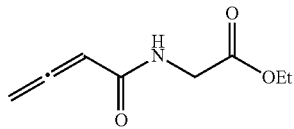

3-Butynoic acid (preparation 1, 0.34 g, 1 eq., 4.04 mmol) and 1.55 g of 2-chloro-1-methyl pyridinium iodide (1.5 eq., 6.06 mmol) were charged in a 25 mL two neck oven dried RBF fitted with a magnetic stirrer bar. 15 mL dry dichloromethane was added to it and the mixture was stirred under nitrogen for 1 hr. A solution of 0.62 g of glycine ethyl ester hydrochloride (1.1 eq., 4.45 mmol) and 1.6 mL triethylamine (2.5 eq., 11.25 mmol) in 5 mL dry dichloromethane was added to it drop wise after which the reaction mixture was stirred for another half an hour. After the work up as described above, product was purified by flash column chromatography (20% EA in hexane) to get 0.4321 g of 6 (2.56 mmol; 63% yield). (The product was collected in two fractions varying slightly in rf values. The first fraction (0.19 g) was found to contain 20% of homopropargylic isomer while the second fraction (0.24 g) was pure allenic isomer).

$^1$H NMR (400 MHz, CDCl$_3$) δ 6.71 (s, 1H), 5.71 (t, 1H, J=6.59 Hz), 5.26 (d, 2H, J=6.64 Hz), 4.21 (q, 2H, J=7.16 Hz), 4.06 (d, 2H, J=5.44 Hz), 1.29 (t, 3H, J=7.15); $^{13}$C NMR (400 MHz, CDCl3) δ 212.3, 169.9, 164.8, 90.2, 80.6, 61.4, 41.4, 14.1; ESI-MS calculated for C$_8$H$_{11}$NO$_3$ [M+H]$^+$ m/z 169.07. found 169.09.

Synthesis of N-cyclohexylbuta-2,3-dienamide (1c)

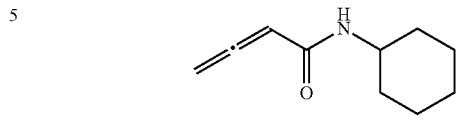

3-Butynoic acid (preparation 1, 0.10 g, 1 eq., 1.21 mmol) and 0.46 g of 2-chloro-1-methyl pyridinium iodide (1.5 eq., 1.82 mmol) were charged in a 25 mL two neck oven dried RBF fitted with a magnetic stirrer bar. 6 mL dry dichloromethane was added to it and the mixture was stirred under nitrogen for 1 hr. A solution of 0.15 mL of cyclohexylamine (1.1 eq., 1.33 mmol) and 0.28 mL triethylamine (1.5 eq., 2.00 mmol) in 4 mL dry dichloromethane was added to it drop wise after which the reaction mixture was stirred for another half an hour. After the work up as described above, product was purified by flash column chromatography (20% EA in hexane) to get 0.1143 g of 7 (28% homopropargylic and 72% allenic isomers as separate fractions) (0.69 mmol; 57% yield).

Homopropargylic Isomer:

$^1$H NMR (300 MHz, CDCl3) δ 6.38 (s, 1H) 3.81-3.72 (m, 1H) 3.19 (d, 2H, J=2.68 Hz), 2.37 (t, 1H, J=2.7 Hz), 1.94-1.89 (m, 2H), 1.72 (td, 2H, J=3.7, 13.5 Hz), 1.62 (td, 1H, J=3.7, 13.0 Hz), 1.44-1.33 (m, 2H), 1.24-1.15 (m, 3H); $^{13}$C NMR (300 MHz, CDCl3) δ 165.0, 77.7, 74.0, 48.4, 32.8, 27.5, 25.5, 24.7; ESI-MS calculated for C$_{10}$H$_{15}$NO [M+H]$^+$ m/z 165.12. found 165.09.

Allenic Isomer (1c):

$^1$H NMR (300 MHz, CDCl3) δ 5.74 (s, 1H), 5.61 (t, 1H, J=6.7 Hz), 5.21 (d, 2H, J=6.7 Hz), 3.83-3.75 (m, 1H), 1.95-1.92 (m, 2H), 1.72-1.60 (m, 3H), 1.42-1.33 (m, 2H), 1.22-1.10 (m, 3H); $^{13}$C NMR (300 MHz, CDCl3) δ 211.5, 163.5, 91.2, 80.3, 48.3, 33.1, 25.5, 24.8; ESI-MS calculated for C$_{10}$H$_{15}$NO [M+H]$^+$ m/z 165.12. found 165.10.

Synthesis of N-(naphthalene-1-yl)buta-2,3-dienamide (1d)

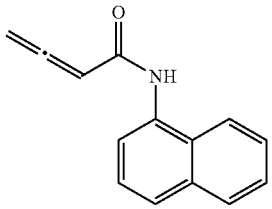 [SMILES: C=C=CC(=O)Nc1cccc2ccccc12]

3-Butynoic acid (preparation 1, 0.11 g, 1 eq., 1.27 mmol) and 0.48 g of 2-chloro-1-methyl pyridinium iodide (1.5 eq., 1.90 mmol) were charged in a 15 mL two neck oven dried RBF fitted with a magnetic stirrer bar. 6 mL dry dichloromethane was added to it and the mixture was stirred under nitrogen for 1 hr. A solution of 0.16 g of 1-naphthylamine (0.9 eq., 1.14 mmol) and 0.24 mL triethylamine (1.5 eq. respective to naphthylamine, 1.71 mmol) in 4 mL dry dichloromethane was added to it drop-wise after which the reaction mixture was stirred for another half an hour. After the work up as described above, product was purified by flash column chromatography (25% EA in hexane) to get 0.067 g of light brown solid which was found to be the homopropargylic isomer of 8. However, it was readily isomerized to 8 by treating with 1 eq. of triethylamine in dichloromethane (1 mL).

$^1$H NMR (400 MHz, CDCl$_3$) δ 8.01 (s, 1H), 7.87 (dd, 1H, J=6.9, 2.4 Hz), 7.80 (d, 1H, J=6.8 Hz), 7.70 (d, 1H, J=8.3 Hz), 7.55-7.46 (m, 4H), 5.89 (t, 1H), 5.45 (d, 2H, J=4.8 Hz); $^{13}$C NMR (400 MHz, CDCl$_3$) δ 211.8, 162.8, 134.1, 132.1, 128.9, 126.9, 126.4, 126.0, 125.9, 120.2, 92.0, 81.4; ESI-MS calculated for C$_{14}$H$_{11}$NO [M+H]$^+$ m/z 209.08. found 209.06.

Synthesis of N-(2-oxo-4-(trifluoromethyl)-2H-chromen-7-yl)buta-2,3-dienamide (1e)

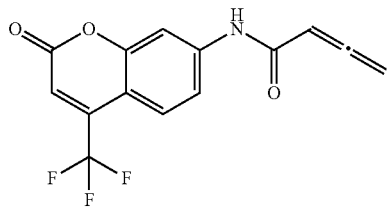 [SMILES: C=C=CC(=O)Nc1ccc2c(C(F)(F)F)cc(=O)oc2c1]

3-Butynoic acid (preparation 1, 0.27 g, 1 eq., 3.2 mmol) and 1.22 g of 2-chloro-1-methyl pyridinium iodide (1.5 eq., 4.8 mmol) were charged in a 25 mL two neck oven dried RBF fitted with a magnetic stirrer bar. 10 mL dry dichloromethane was added to it and the mixture was stirred under nitrogen for 1 hr. 0.66 g of respective amine (7-amino-4-(trifluoromethyl)-2H-chromen-2-one) was added (0.9 eq. 2.9 mmol) in portions (solid) followed by addition of 0.60 mL of triethylamine (1.5 eq. respective to amine, 4.3 mmol) in 5 mL dry dichloromethane after which the reaction mixture was stirred for another half an hour. After due time dichloromethane was evaporated and product was purified by flash column chromatography (30-40% EA in hexane) to get a yellow solid.

$^1$H NMR (400 MHz, CDCl$_3$) δ 7.84 (s, 1H), 7.81 (d, 1H, J=2.1 Hz), 7.66 (dd, 1H, J=1.7, 8.9 Hz), 7.49 (dd, 1H, J=2.1, 8.8 Hz), 6.70 (s, 1H), 5.82 (t, 1H, J=6.6 Hz), 5.46 (d, 2H, J=6.6 Hz); $^{13}$C NMR (400 MHz, CDCl$_3$) δ 212.2, 162.6, 159.1, 155.3, 142.1, 126.1, 126.0, 115.9, 113.9, 113.8, 109.5, 107.2, 91.7, 82.1; ESI-MS calculated for C$_{14}$H$_8$F$_3$NO$_3$ [M+H]$^+$ m/z 296.05. found 296.16.

Synthesis of tert-butyl (2-(buta-2,3-dienamido)ethyl)carbamate (1f)

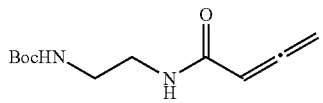 [SMILES: C=C=CC(=O)NCCNC(=O)OC(C)(C)C]

Above mentioned procedure was used utilizing 0.38 gm of 3-butynoic acid (preparation 1, 4.5 mmol), 1.74 gm of Mukaiyama reagent (1.5 eq., 6.8 mmol), 0.8727 gm of N-Boc-Ethylenediamine (see above; 1.2 eq., 5.4 mmol) and 0.6 mL triethylamine. 0.3833 gm of product was obtained (1.7 mmol, 38% yield).

$^1$H NMR (400 MHz, CDCl3) δ 6.79 (s, 1H), 5.64 (t, 1H, J=6.6 Hz), 5.31 (s, 1H), 5.22 (d, 2H, J=6.6 Hz), 3.42-3.38 (m, 2H), 3.29 (t, 2H, J=5.5 Hz), 1.44 (s, 9H); $^{13}$C NMR (400 MHz, CDCl3) δ 211.9, 165.3, 156.8, 90.5, 80.3, 79.4, 73.9, 40.8, 40.1, 28.2, 27.2

Synthesis of N-(2-aminoethyl)buta-2,3-dienamide (1g)

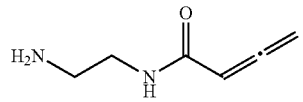

Compound was synthesised from 1f following procedure in Liu, F. et al., *Bioconjugate Chemistry* 2012, 23, 1639.

$^1$H NMR (400 MHz, MeOD) δ 8.10 (s, 1H), 5.75 (t, 1H, J=6.6 Hz), 5.32 (d, 2H, J=6.6 Hz), 3.55 (t, 2H, J=5.8 Hz), 3.12 (t, 2H, J=5.8 Hz); $^{13}$C NMR (400 MHz, MeOD) δ 213.0, 167.2, 89.0, 79.2, 39.4, 37.1; ESI-MS calculated for C$_6$H$_{10}$N$_2$O [M+H]$^+$ m/z 127.08. found 126.99.

Table 1 lists the C-substituted Allenamides 1a to 1f synthesised from corresponding amines

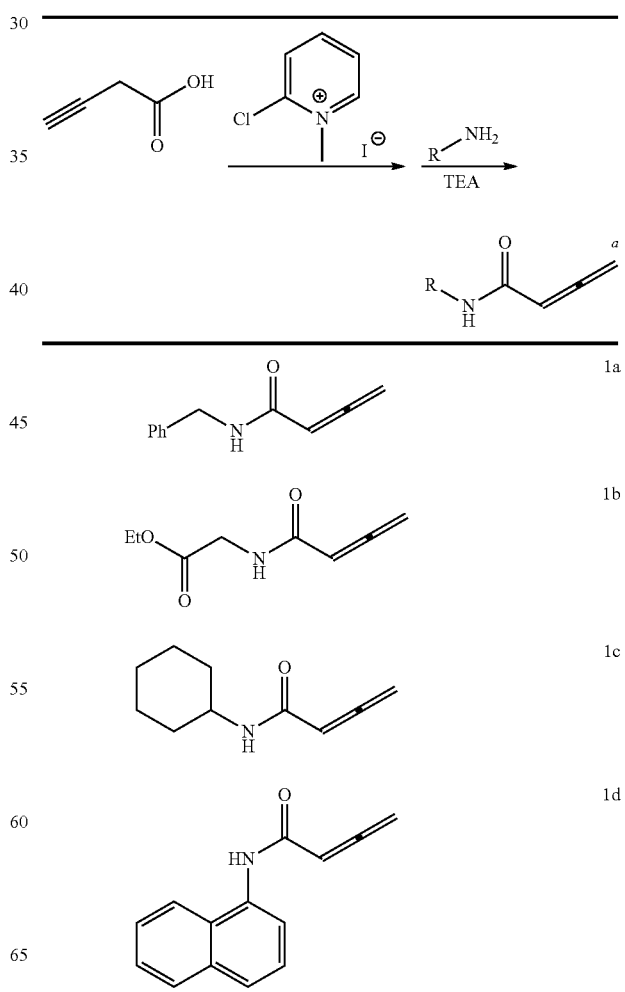

-continued

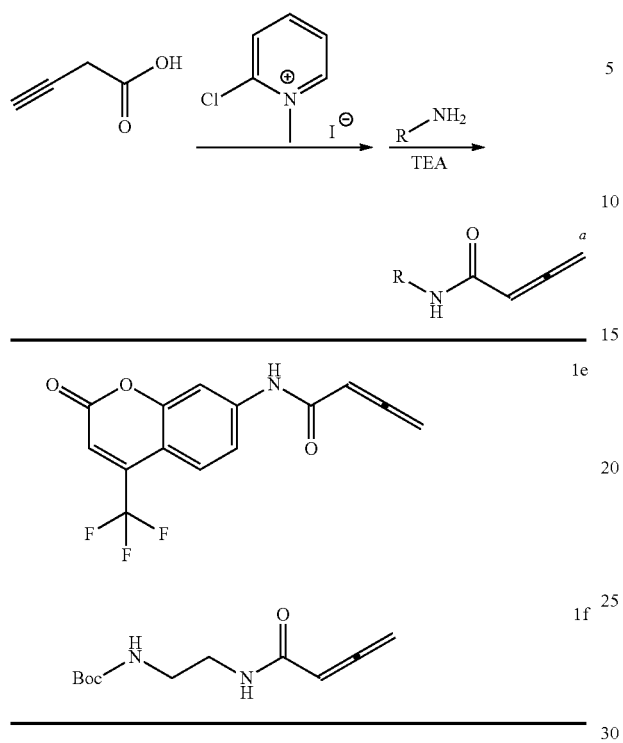

<sup>a</sup>A small amount of homopropargyl amide is also observed sometimes which can be isomerized to allenic isomer by excess TEA

Synthesis of Fluorescence Isomer I Having Allenamide Handle (6)

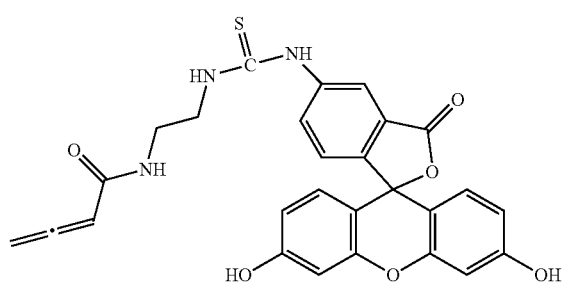 [SMILES: C=C=CC(=O)NCCNC(=S)Nc1ccc2c(c1)C(=O)OC21c2ccc(O)cc2Oc2cc(O)ccc21]

50 mg of FITC (Fluorescein isothiocyanate) isomer I (1 eq. 0.13 mmol) was dissolved in 0.5 mL DMF in a 1.5 mL glass vial. To it was added 24 mg of 1g (1.5 eq., 0.19 mmol) dissolved in 0.5 mL DMF and 34 μL of DIPEA (N,N-Diisopropylethylamine) one by one and the reaction mixture was stirred in dark for 2 hrs. LCMS after 2 hrs showed the formation of the desired compound. Reaction mixture was directly loaded on silica gel column and product was eluted with 25% MeOH in dichloromethane.

$^1$H NMR (400 MHz, MeOD) δ 8.02 (d, 2H, J=1.7 Hz), 7.70 (dd, 1H, J=2.0, 8.2 Hz), 7.24-7.14 (m, 4H), 6.64 (m, 6H), 5.71 (t, 1H, J=6.6 Hz), 5.28 (d, 2H, J=6.6 Hz), 3.81 (t, 2H, J=5.7 Hz), 3.57-3.47 (m, 4H); ESI-MS calculated for $C_{27}H_{21}N_3O_6S$ [M+H]$^+$ m/z 516.12. found 516.23.

Synthesis of Cy3 (Cyanine 3) Having Allenamide Handle (7)

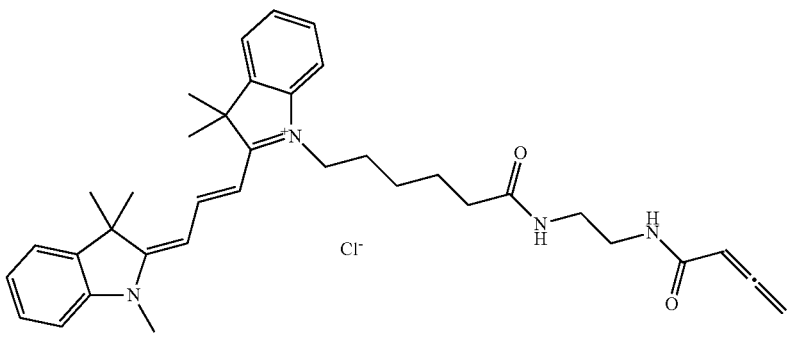 [SMILES: C=C=CC(=O)NCCNC(=O)CCCCC[N+]1=C(/C=C/C=C2/N(C)c3ccccc3C2(C)C)C(C)(C)c2ccccc21 ; [Cl-]]

5.0 mg of Cy3-NHS ester (1 eq., 8.5 μmol) was dissolved in 250 μL of DMF in a 1.5 mL glass vial. To it was added 2.1 mg of 1g (2 eq., 17 μmol) dissolved in 250 μL of DMF followed by 3 μL of DIPEA (2 eq., 17 μmol). Reaction mixture was stirred in dark for 2 hrs after which LCMS showed the formation of the desired product which was purified on reverse phase HPLC using a C-18 preparative column and water/ACN solvent system having 0.1% TFA.

$^1$H NMR (400 MHz, MeOD) δ 8.58 (t, 3H, J=13.6), 8.04 (s, 1H), 7.57 (d, 2H, J=7.3 Hz), 7.50-7.46 (m, 2H), 7.39-7.28 (m, 4H), 7.14-7.04 (m, 1H), 6.47 (dd, 2H, J=2.9, 13.5 Hz), 5.68 (t, 1H, J=6.6 Hz), 5.26 (d, 2H, J=6.6 Hz), 4.18 (t, 2H, J=7.5 Hz), 3.78 (t, 1H, J=7.1), 3.71 (s, 2H), 2.24 (t, 2H, J=7.2 Hz), 1.92-1.84 (m, 2H), 1.79 (s, 6H), 1.73 (t, 2H, J=7.5), 1.60 (s, 1H), 1.54-1.47 (m, 3H), 1.40-1.27 (m, 6H); ESI-MS calculated for $C_{36}H_{45}ClN_4O_2$ [M-Cl+H]$^+$ m/z 565.35. found 565.62.

Synthesis of Sulfo-Cy5 (Cyanine 5) Having Allenamide Handle (8)

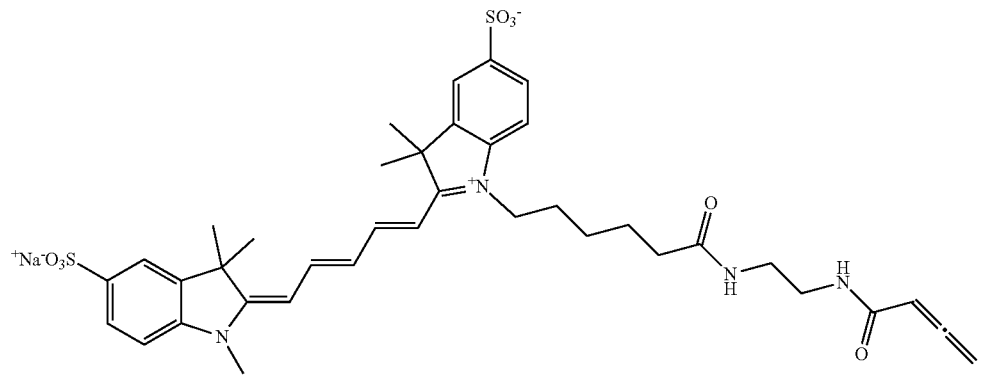

2.5 mg of Sulfo-Cy5-NHS ester (1 eq., 3.8 μmol) was dissolved in 200 μL of DMF in a 1.5 mL glass vial. To it was added 0.9 mg of 1g (2 eq., 7.6 μmol) dissolved in 100 μL of DMF followed by 1.3 μL of DIPEA (2 eq., 7.6 μmol). Reaction mixture was stirred in dark for two hrs. Product was purified on reverse phase HPLC using a C-18 preparative column and water/ACN solvent system having 0.1% TFA.

$^1$H NMR (400 MHz, D$_2$O) δ 7.99 (t, 2H, J=13.0 Hz), 7.80-7.73 (m, 4H), 7.27 (dd, 2H, J=8.6, 11.4 Hz), 6.51 (t, 1H, J=12.9), 6.27-6.19 (m, 2H), 5.58 (t, 1H, J=6.6 Hz), 5.11 (d, 2H, J=6.6 Hz), 4.03 (m, 4H), 3.16-3.11 (m, 4H), 2.15 (s, 1H), 2.13-2.11 (m, 2H), 1.76 (m, 2H), 1.61 (s, 12H), 1.53 (m, 2H), 1.29 (t, 3H, J=7.3 Hz), 1.25 (m, 2H). ESI-MS calculated for C$_{38}$H$_{45}$N$_4$NaO$_8$S$_2$[M−Na+2H]$^+$ m/z 751.28. found 751.47.

Peptide Synthesis

Peptides CGKSRF (3), KSCGRF (4) and YDSQCFHRW (5) were synthesized on the automated Liberty 1 CEM Microwave Peptide Synthesizer fitted with UV monitor using preloaded wang resin and following standard protocol. Peptides were characterized by LCMS and were used without further purification.

Example 1

Modification of Cysteine Methyl Ester Using 1a to Provide 1aa

To a solution of allenamide 1a (0.122 mmol; 21.2 mg in 0.4 mL THF) was added a mixture of cysteine methyl ester hydrochloride (0.122 mmol; 21.0 mg) and potassium carbonate (0.125 mmol; 17.3 mg) in 1.6 mL water. Reaction mixture was stirred for 30 minutes after which TLC confirmed the complete consumption of 1a. THF was evaporated on rotary evaporator and product was extracted two times in dichloromethane (2.5 mL each). Solvent was evaporated and product was purified by column chromatography (5% MeOH in dichloromethane) to get 32.8 mg (76% yield) of white solid (modified cysteine).

$^1$H NMR (400 MHz, CDCl3) δ 7.35-7.25 (m, 5H), 6.69 (s, 1H), 5.33 (s, 1H), 5.11 (s, 1H), 4.51-4.40 (m, 2H), 3.70 (s, 3H), 3.69 (t, 1H, J=4.5 Hz), 3.23 (d, 2H, J=2.5 Hz), 3.17 (dd, 1H, J=4.7, 13.7 Hz), 2.94 (dd, 1H, J=7.7, 13.8 Hz), 1.65 (s, 2H); $^{13}$C NMR (400 MHz, CDCl3) δ 174.13, 168.85, 138.25, 137.83, 128.64, 127.68, 127.43, 112.76, 53.44, 52.40, 45.16, 43.62, 36.12; ESI-MS calculated for C$_{15}$H$_{20}$N$_2$O$_3$S [M+H]$^+$ m/z 309.13. found 309.10.

Figure 2:
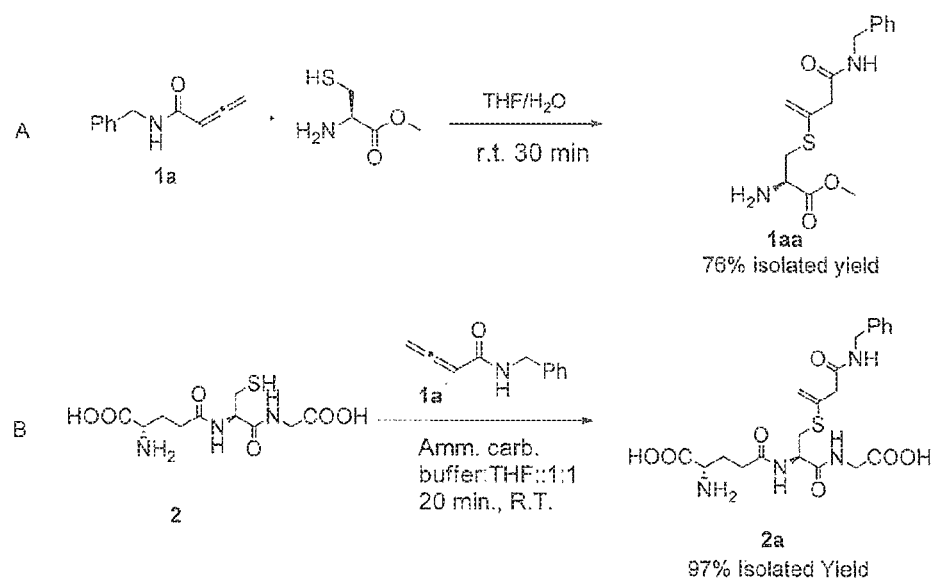
FIG. 2 depicts reactions of allenamide 1a with Cysteine methyl ester (A) and Glutathione (B).

The reaction of benzyl allenamide 1a with a cysteine methyl ester containing free thiol and amino groups is shown in FIG. 2A. No reaction was observed at the free amino group even when 1a was used in excess. Only the free thiol group was found to be involved in the reaction, giving product 1aa. At the same time, no product was obtained when 1a was reacted with lysine, serine and methionine amino acids under similar conditions, confirming that the reaction of allenamide with a thiol group is selective under the conditions used.

Example 2

Modification of Glutathione (2) Using Allenamide 1a to Provide 2a 6.5 mg glutathione (0.021 mmol) was dissolved in 0.5 mL ammonium carbonate buffer (pH 8.0) in a 4 mL glass vial. To this solution was added 7.3 mg of allenamide 1a (0.042 mmol; 2 eq.) in 0.5 mL THF and resulting solution was mixed well using a pipette. LCMS after 15 min. showed complete conversion of glutathione after which, 3 mL of THF was added to the vial causing the product 2a to precipitate. This mixture was centrifuged at 8000 rpm for 5 min. Liquid was carefully decanted and the solid precipitated was washed two times with THF. The precipitate after final washing was dried in vacuum to give 9.9 mg (97% yield) of white solid (modified glutathione).

$^1$H NMR (400 MHz, D$_2$O) δ 7.36-7.27 (m, 5H), 5.36 (s, 1H), 5.19 (s, 1H), 4.57 (dd, 1H, J=5.0, 8.6), 4.35 (s, 2H), 3.70 (d, 2H, J=8.0), 3.67-3.65 (m, 1H), 3.25 (m, 3H), 3.02 (dd, 1H, J=8.7, 13.9), 2.42 (t, 2H, J=8.0), 2.06 (q, 2H, J=7.6); $^{13}$C NMR (400 MHz, D2O) δ 175.5, 174.9, 173.9, 172.5, 171.8, 138.0, 136.4, 128.8, 127.5, 127.3, 115.2, 54.2, 52.5, 44.2, 43.2, 43.0, 32.4, 31.5, 26.2; ESI-MS calculated for C$_{21}$H$_{28}$N$_4$O$_7$S [M+H]$^+$ m/z 481.18. found 481.23.

Figure 3:
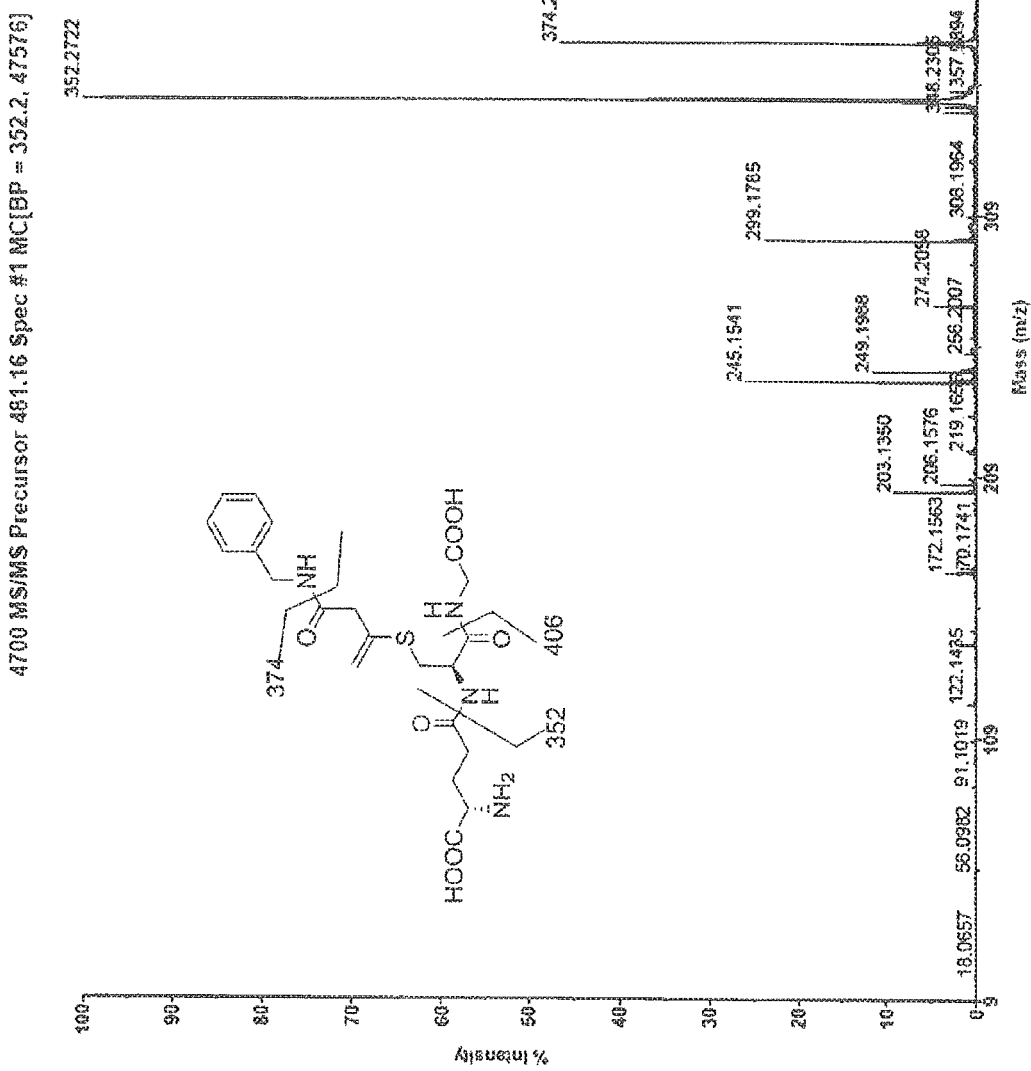
FIG. 3 is an MS spectrum showing MS/MS of modified glutathione.

The naturally occurring tripeptide, glutathione (GSH; 2), was reacted with allenamide 1a shown in FIG. 2B. The desired product 2a was obtained in 97% isolated yield and characterized by NMR and LC-MS/MS confirming the modification at the cysteine residue (i.e. the thiol group) instead of amino groups in the peptide residues, suggesting excellent reaction selectivity of C-substituted terminal allenamides to the specific cysteine conjugation (FIG. 3).

Example 3

General Procedure for the Modification of Peptides 3, 4 and 5 with Allenamide 1a To further demonstrate selectivity, cysteine modification of three other peptide sequences including Cys-Gly-Lys-Ser-Arg-Phe (3), Lys-Ser-Cys-Gly-Arg-Phe (4) and Tyr-Asp-Ser-Gln-Cys-Phe-His-Arg-Trp (5) with terminal as well as internal cysteine residues was also investigated.

100 µL of the peptide solution (250 µM in ammonium carbonate buffer of pH 8.0) was mixed with an equal amount of the solution of 1a (2.5 mM in ammonium carbonate buffer containing 5% THF). After pipette mixing, reaction mixture was allowed to stand at room temperature for 10-20 minutes. LCMS was done to ensure complete conversion. Site selectivity was established by LC-MS/MS.

Figure 4:
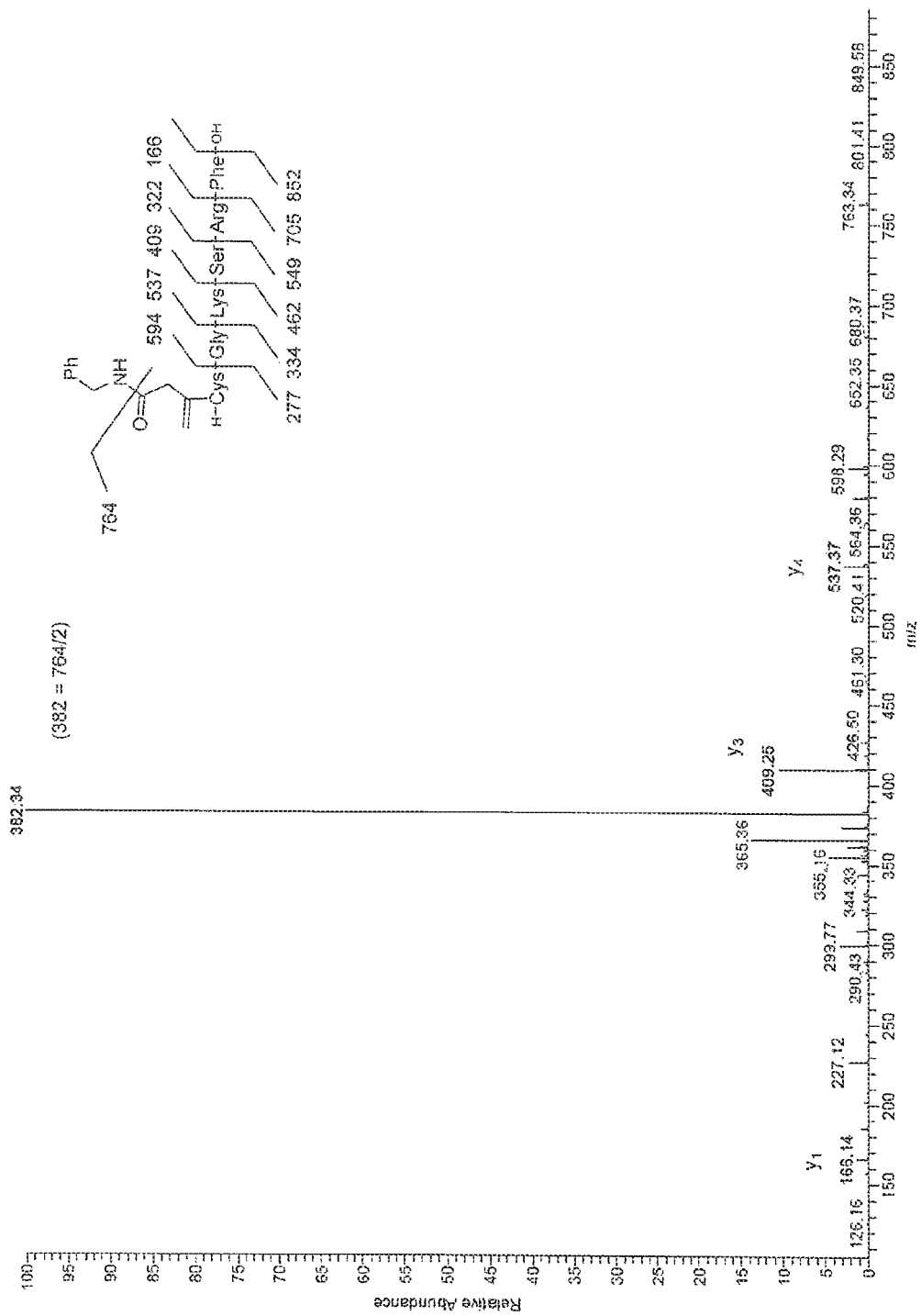
Figure 5:
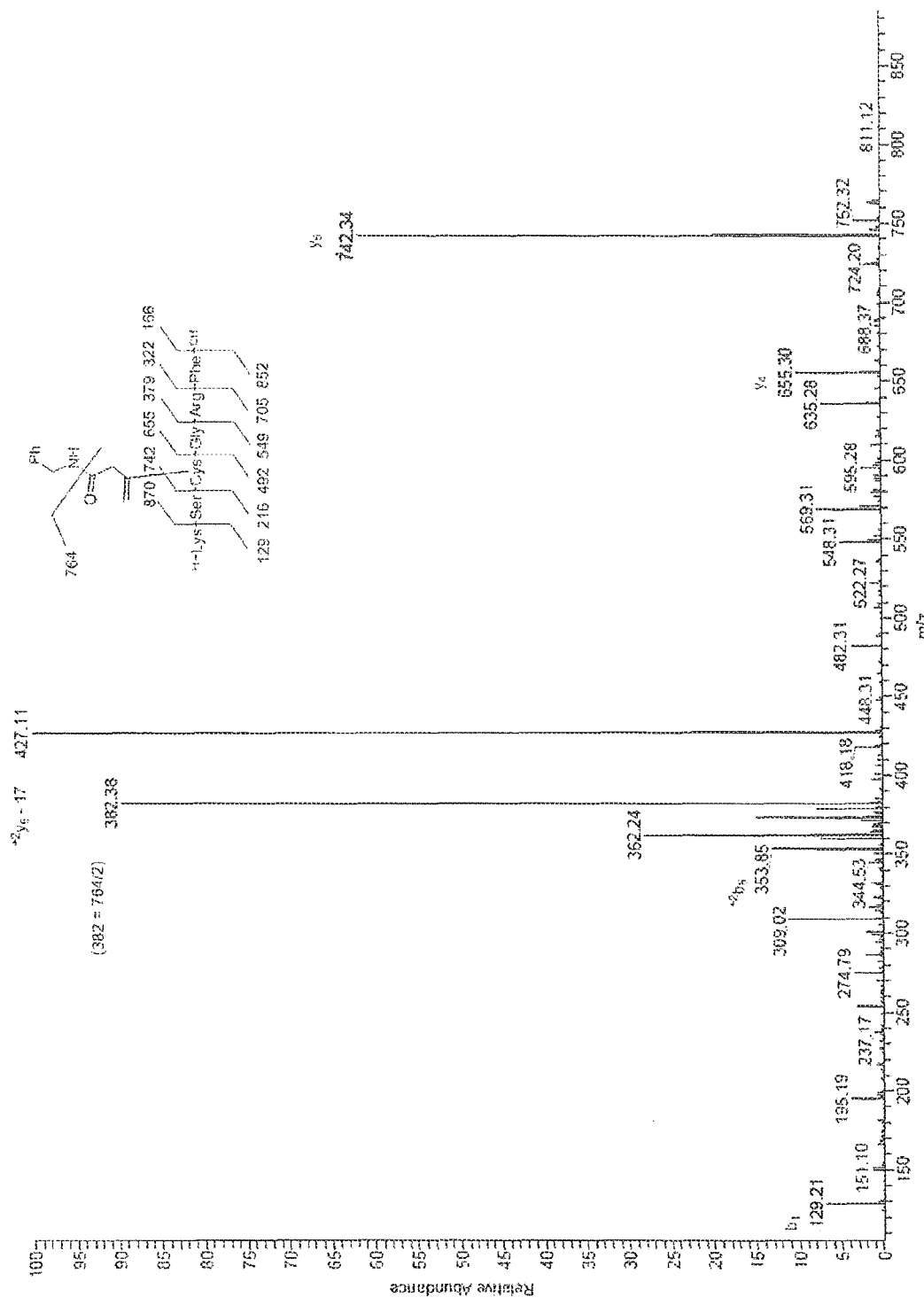
Figure 6:
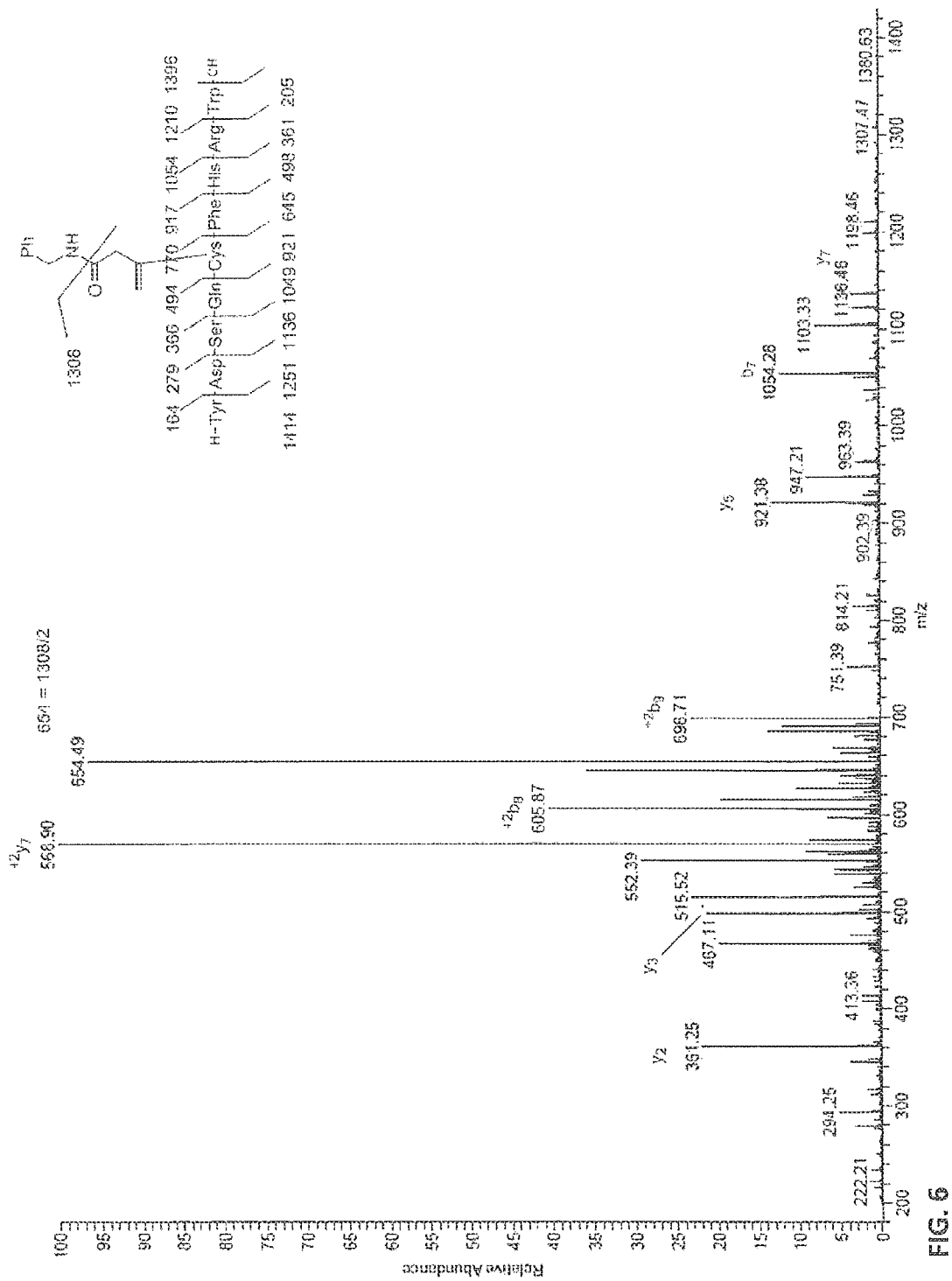

In all cases, quantitative conversion was obtained on incubating the peptide as described above. LCMS and LC-MS/MS analysis (FIGS. 4-6) confirmed the modification to have taken place selectively at cysteine. It should be noted that other amino acid residues including histidine, lysine, tyrosine and other reactive side chains did not give any reaction with 1a even after standing for overnight. The irreversibility of the conjugation product was tested with peptide 5 and GSH (2). No reversion to starting material 5 was observed when the conjugation product of 5 and 1a was incubated with excess (100 equivalent) glutathione for overnight at 37° C. Similarly, the treatment of 2a with excess (100 equivalent) DTT did not produce 2 (LCMS), clearly suggesting the stability of the conjugated products. The irreversibility of specific cysteine labelling may thus enable the possibility for the protein modification in intracellular environment.

Example 4

Figure 7:
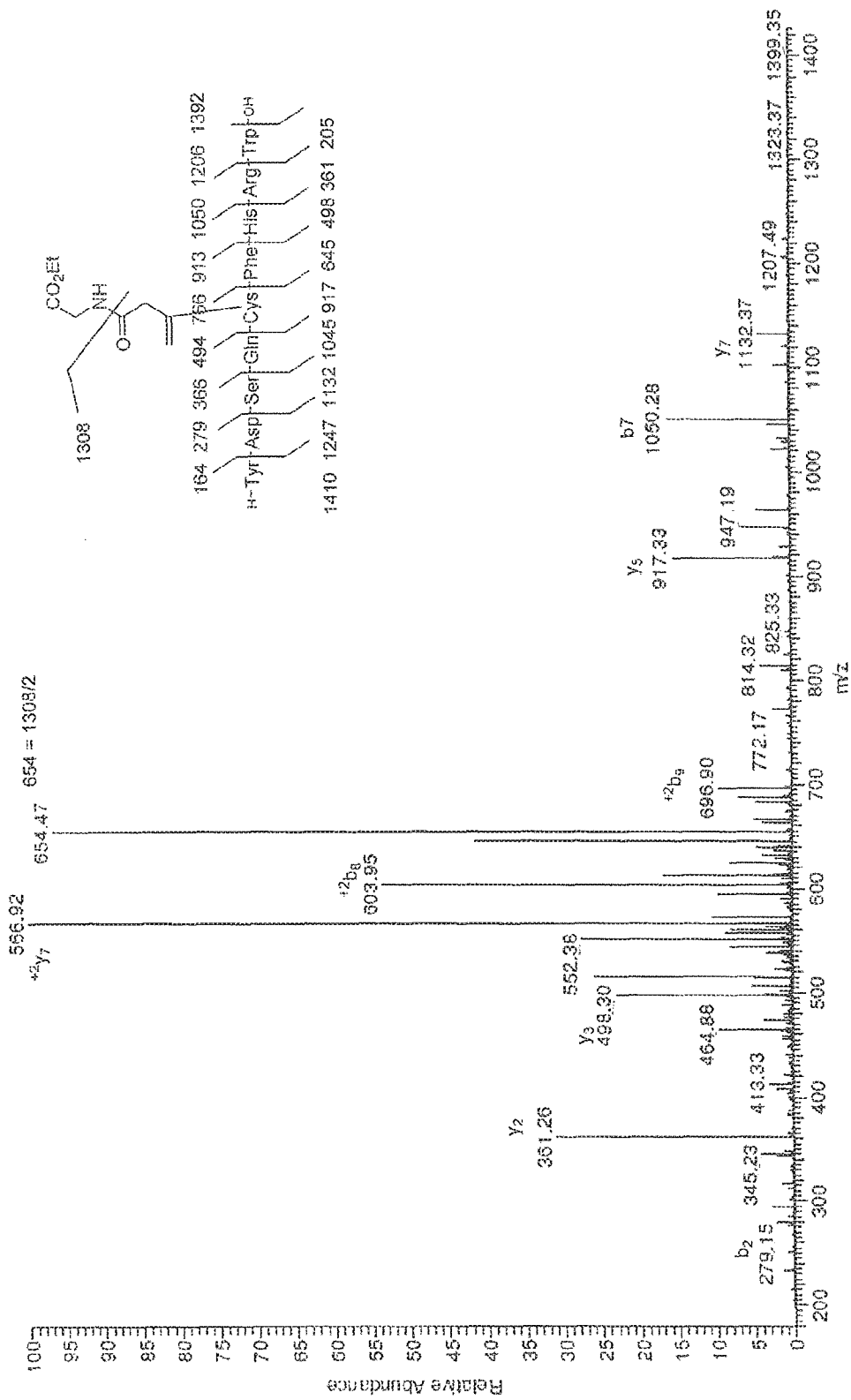
FIG. 7 is an MS spectrum showing MS/MS of peptide YDSQCFHRW modified with allenamide 1b.
Figure 8:
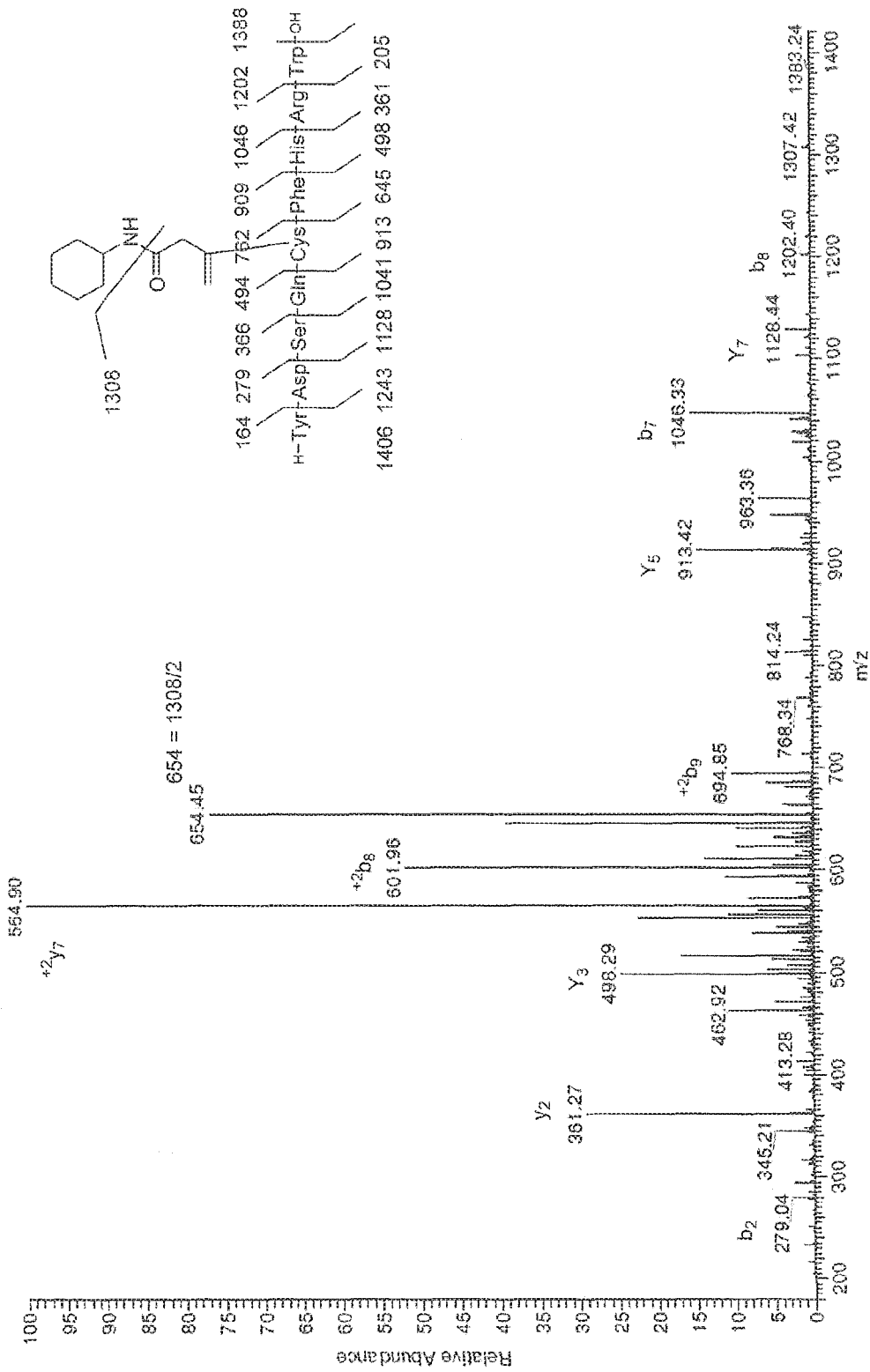
FIG. 8 is an MS spectrum showing MS/MS of peptide YDSQCFHRW modified with allenamide 1c.
Figure 9:
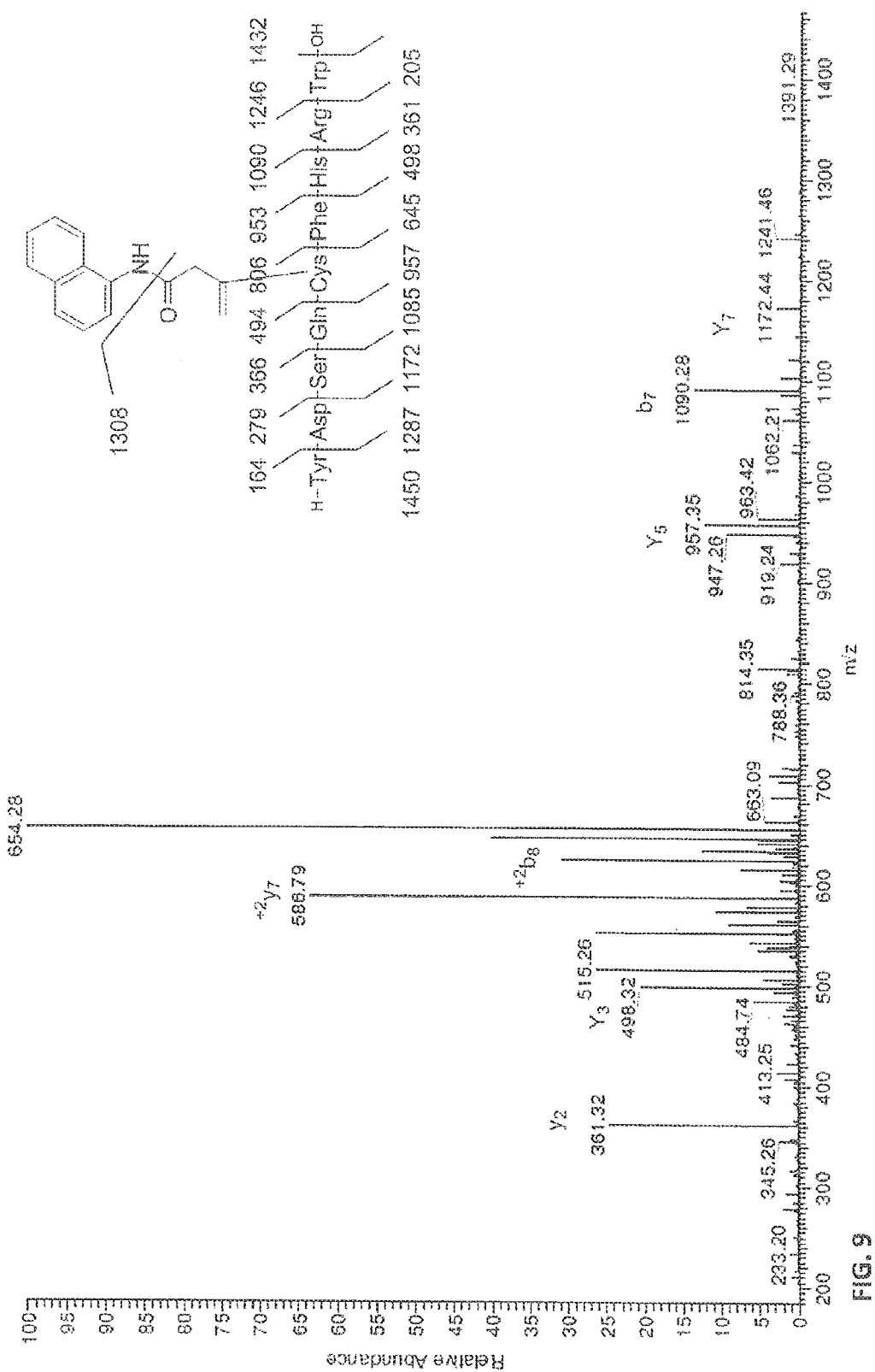
FIG. 9 is an MS spectrum showing MS/MS of peptide YDSQCFHRW modified with allenamide 1d.

Modification of Peptide 5 with Compounds 1b-1d 1b-d were used to modify peptide 5 giving quantitative conversion and excellent selectivity in each case (see Table 2 and FIGS. 7-9).

TABLE 2

Modification of Cysteine in Peptide 5 Using Allenamides 1b-d

| Entry | Allenamide | peptide sequence | Conversion[a] |
|---|---|---|---|
| 1 | 1b | YDSQCFHRW | Quantitative |
| 2 | 1c | YDSQCFHRW | Quantitative |
| 3 | 1d | YDSQCFHRW | Quantitative |

[a]As determined by LCMS

Example 5

Modification of Insulin Using 1a

Figure 10:
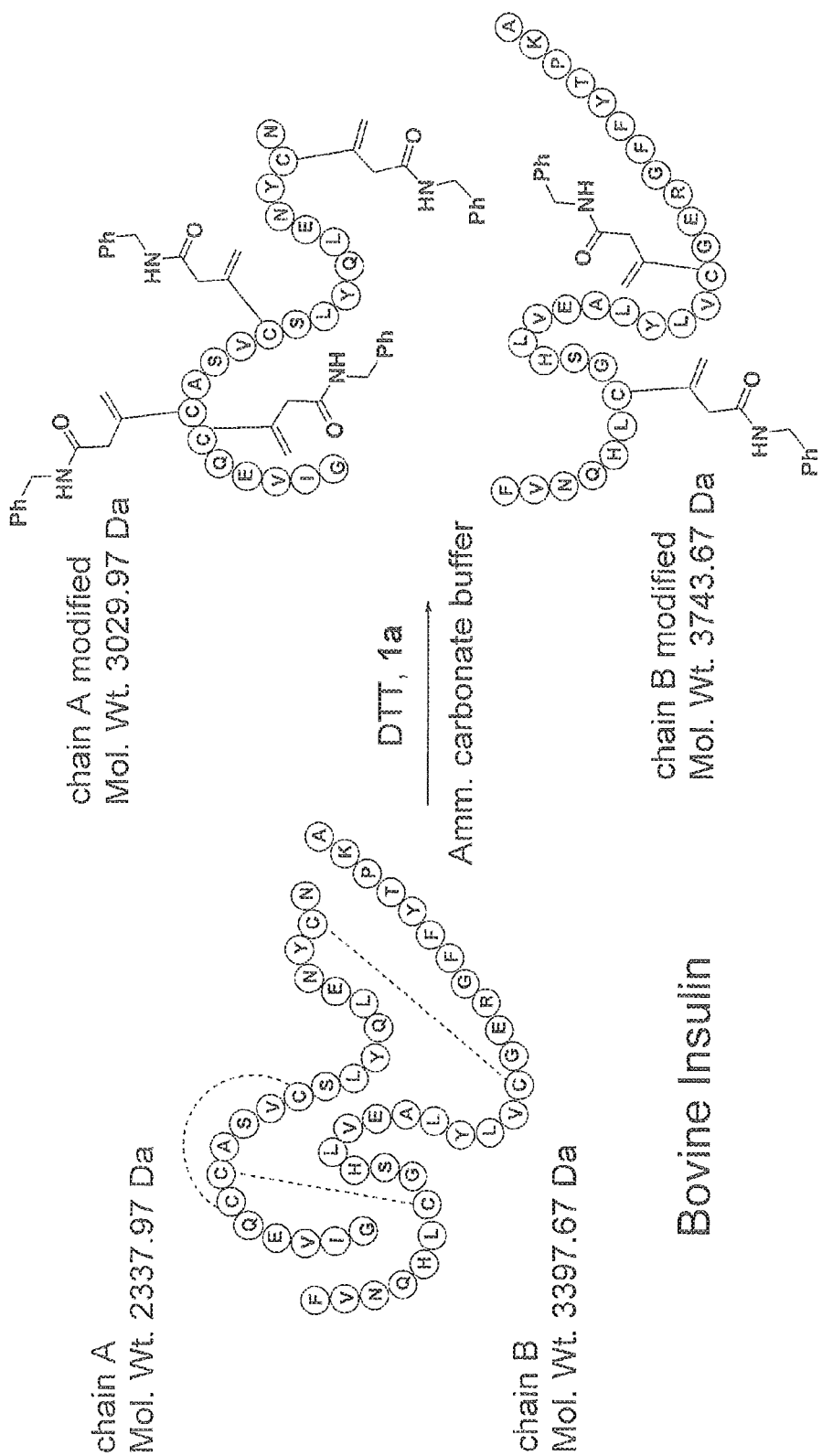

After promising results in simple peptides, similar modification of cysteine residue in more complicated peptide sequences was also examined. A more complex pair of peptides generated from the DTT treatment of bovine insulin was tested (FIG. 10).

Figure 11:
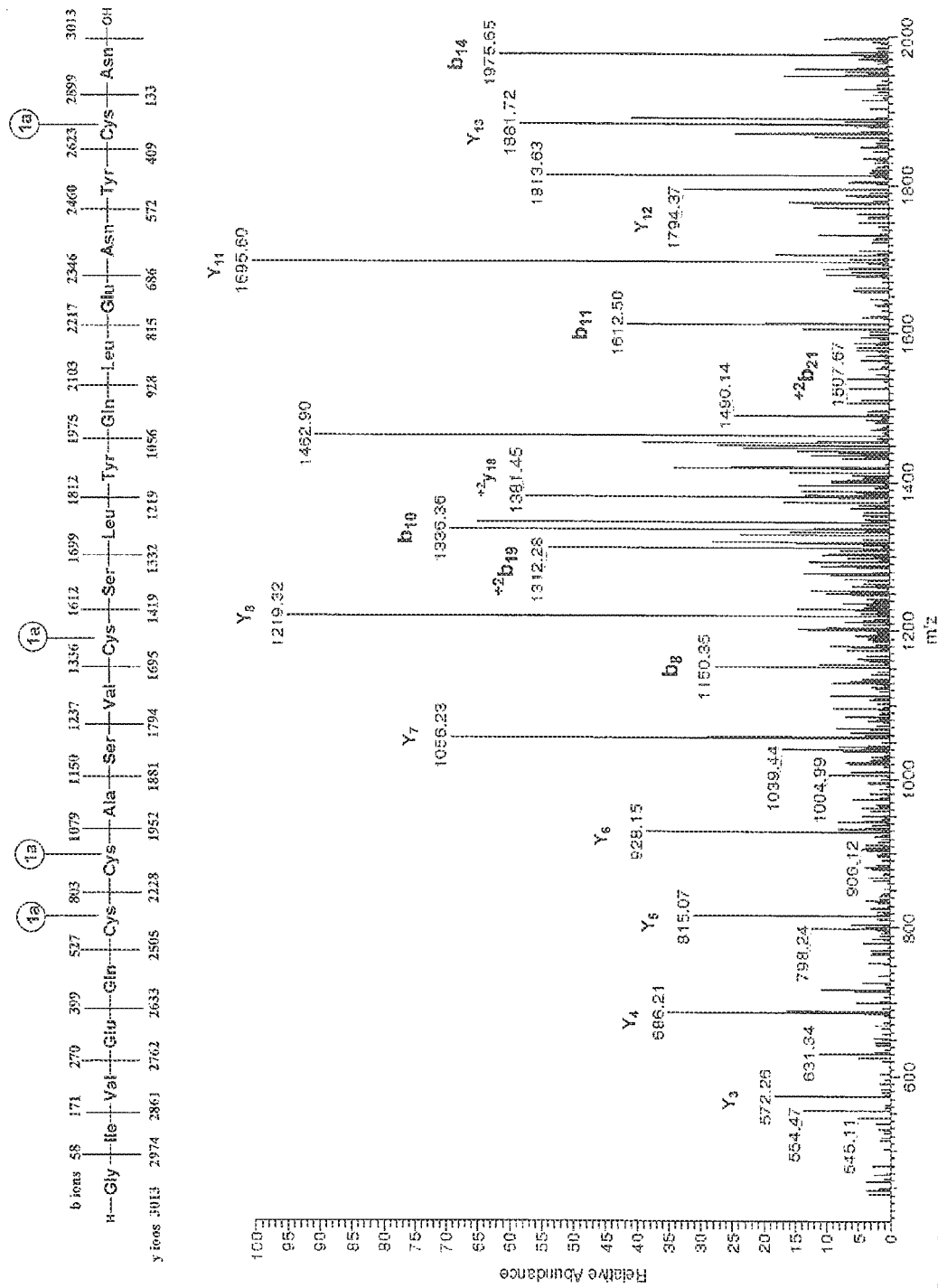
Figure 12:
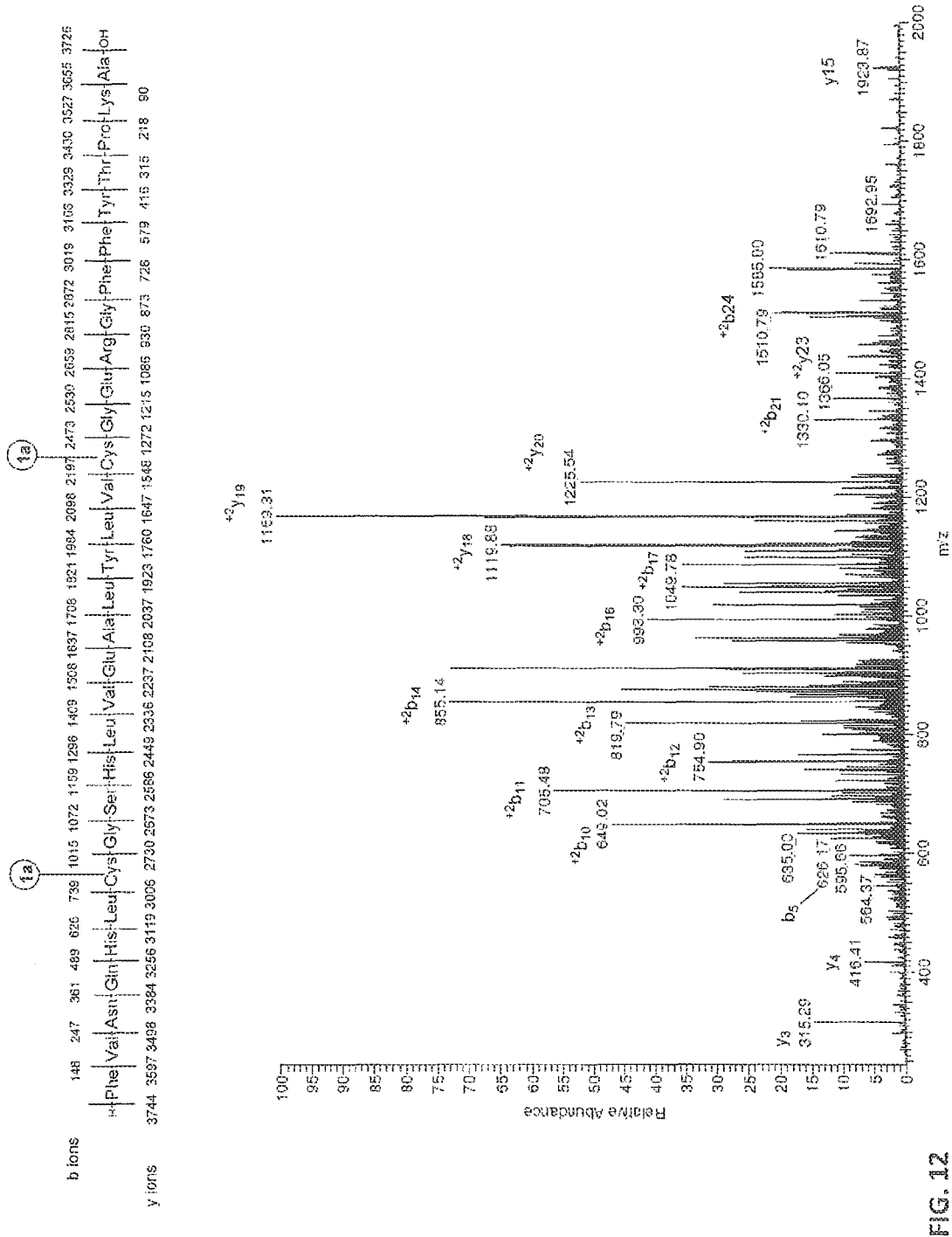

10 equivalents of solid DTT was added to 2 ml of a 10 mM solution of bovine insulin in 50 mM ammonium carbonate buffer of pH 8. The mixture after pipette mixing was allowed to stand at 70° C. under nitrogen atmosphere for 10 minutes. LCMS was done after due time and cooling to room temperature to confirm complete reduction of disulfide bonds. Two separate peaks were observed in the chromatogram corresponding to reduced chain B and chain A. The m/z values corresponding to chain B were obtained as 680, 850, 1133 and 1700 corresponding to +5, +4, +3 and +2 charge on chain B (molecular weight 3397.67). Similarly the m/Z values corresponding to chain A were obtained as 779, 1169 and 2338 corresponding to +3, +2 and +1 charge on chain A (molecular weight 2337.97). To 1 ml of the reduced insulin mixture was added 25 equivalents of 1a dissolved in 500 µL of THF and reaction mixture was allowed to stand at room temperature for 30 min. after pipette mixing. LCMS after 30 min. confirmed expected modification showing two peaks with different rf values corresponding to modified chain B and chain A. The m/z values were in agreement with expected increment in molecular weight of chain B by 346 (173*2=346, showing inclusion of two molecules of 1 having molecular weight 173) and that of chain A by 692 (173*4=692, showing inclusion of four molecules of 1) which were in agreement with the number of cysteine residues in each chain. Thus, the expected molecular weight of modified chain B was 3743.67 (3397.67+346) and that of chain A was 3029.97 (2337.97+692) and the observed m/z values for modified chain B were at 750, 937, 1249 and 1873 corresponding to +5, +4, +3 and +2 charge and for chain A were at 1011 and 1515 corresponding to +3 and +2 charge on the chain. The site selectivity was further confirmed by MS/MS (FIGS. 11 and 12, respectively).

Example 6

Figure 13:
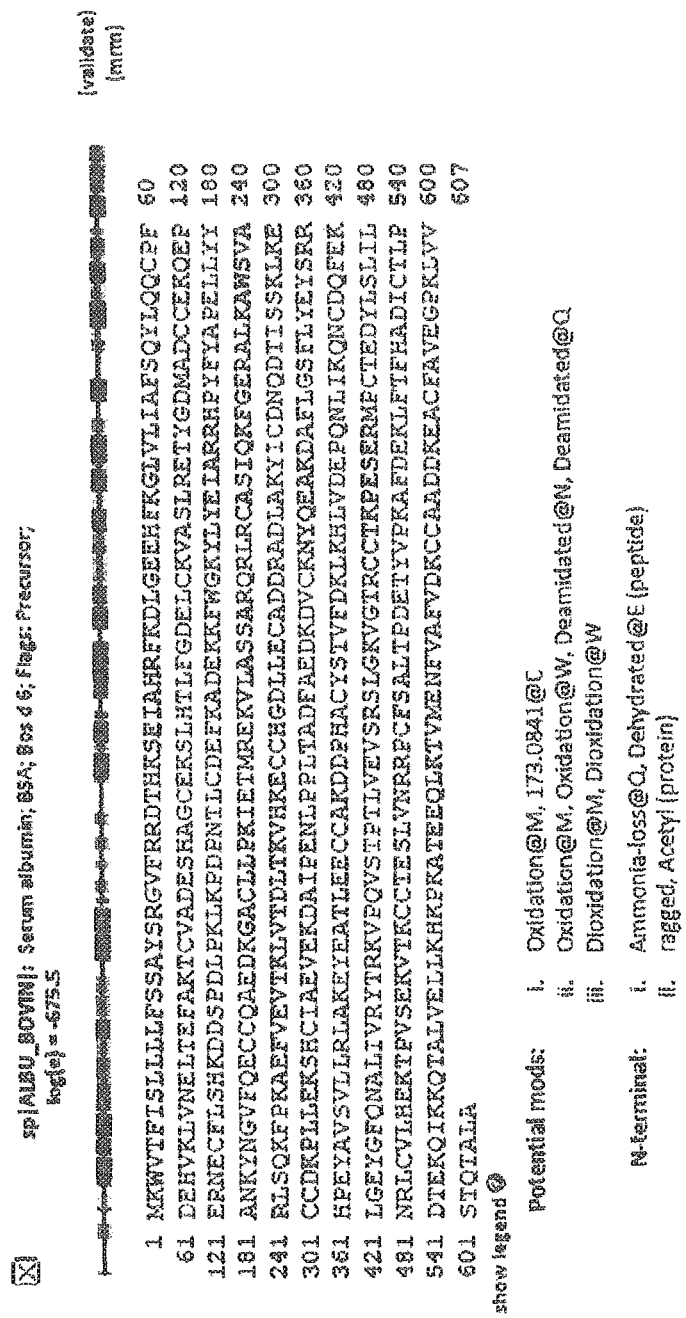

Modification (Alkylation) of BSA with Compound 1a 6.6 mg of BSA (0.1 µmol) was dissolved in 1 ml of ammonium carbonate buffer (pH 8.0). To this was added 2.3 mg solid DTT (15 µmol) and after pipette mixing resulting mixture was incubated over night at 37° C. 3.7 mg of 1a (21 µmol) dissolved in 1 ml of ammonium carbonate buffer (5% THF) was then added to it and incubated again for 30 min at 37° C. After due time, protein was purified through nano-separation filtration. The purified protein was subjected to trypsin digestion and LC-MS/MS using standard protocols (FIG. 13). All cysteine residues in the detected peptides were found to be modified by a molecular weight corresponding to 1a (173.0841).

Example 7

Procedure for Labelling BSA with 6-8

Figure 14:
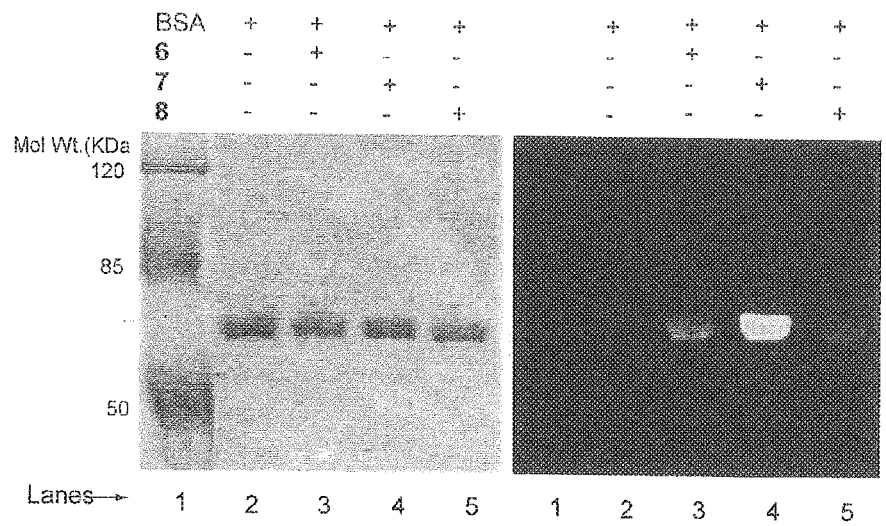
FIG. 14 depicts the labelling of BSA (A) and TEM1 β-Lactamase (B).
Figure 14:
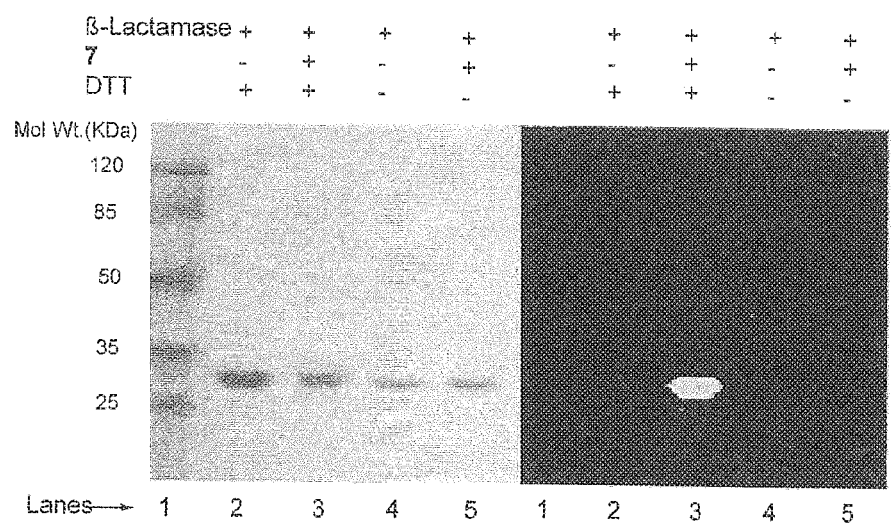

0.1 µmol/mL solution of BSA in $H_2O$ (10 µL, 1 nmol), 1.0 µmol/mL solution of 6, 7 and 8 in $H_2O$ (10 µL each, 10 nmol) and 80 µL of Tris-HCl buffer (pH 7.4) were mixed in 1 mL eppendorf tubes and incubated at 37° C. for 30 min. The resulting solution was then subjected to SDS-PAGE analysis which confirmed desired labelling to have taken place successfully (FIG. 14A).

Example 8

Procedure for Labelling β-Lactamase with 7

For TEM1 β-Lactamase, 0.1 µmol/mL solution of β-Lactamase in $H_2O$ (10 µL, 1 nmol), 1.0 µmol/mL solution of 7 in $H_2O$ (10 µL, 10 nmol) and 80 µL of Tris-HCl buffer (pH 7.4) were mixed in a 1 mL eppendorf tube and incubated at 37° C. for 30 min. After due time, reaction mixture was subjected to SDS-PAGE analysis which confirmed no labelling. In second part of this experiment, 0.1 μmol/mL solution of β-Lactamase (1 mL) was heated with 1.0 μmol/mL solution of DTT (1 mL) at 80° C. for 10 min. After cooling down to room temperature, a 10 μL aliquot of this mixture was mixed with 10 μL of 7 (2.0 μmol/mL in H₂O) and 80 μL of Tris-HCl buffer (pH 7.4) and incubated at 37° C. for 30 min. SDS-PAGE analysis on the resulting mixture revealed successful labelling.

To show that labelling is specific for the thiol group, a well-established antibiotic-resistant bacterial enzyme, TEM 1 β-lactamase (Bla), having only disulfide bonded cystein (no free cysteine) was chosen. Compound 7 was mixed with Bla without DTT treatment and no labeling was observed (lane 5, FIG. 14B) whereas successful labeling was observed when Bla was treated with DTT prior to mixing with 7 (lane 3 FIG. 14B). These results establish allenamide as an efficient handle to target cysteine residue selectively in the complex milieu of protein environment and open an alternative approach for imaging applications.

The invention claimed is:

1. A compound selected from the group consisting of:

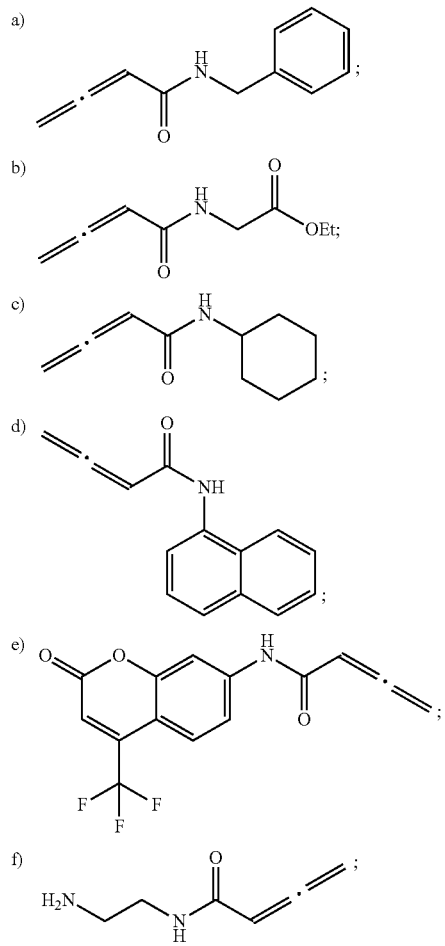

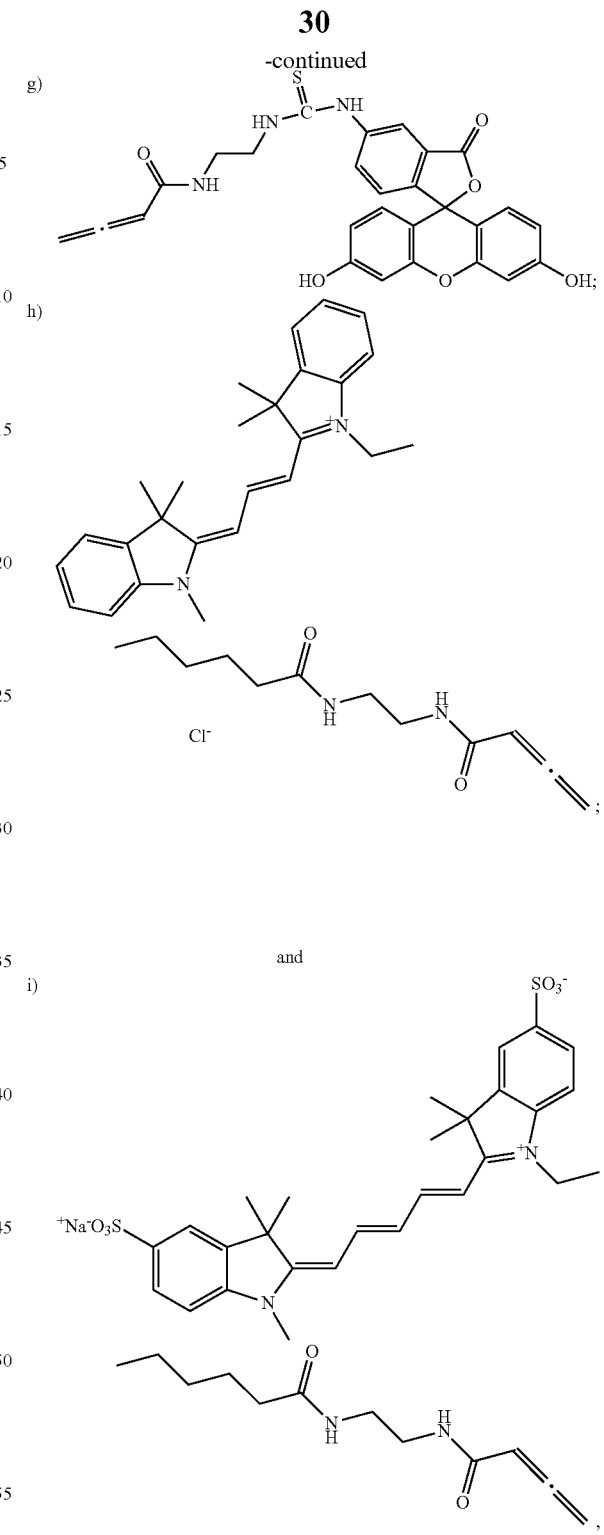

or a pharmaceutically acceptable salt or solvate, or a pharmaceutically functional derivative thereof.

2. The compound according to claim 1, wherein the compound is isotopically labelled.

3. A method of determining the presence or location of a free thiol group in a tissue sample, the method comprising contacting the tissue sample with a compound according to claim 1, as an irreversible binder to the free thiol group.

4. The method of claim 3, wherein the free thiol group is part of a peptide or a protein.

5. A compound according to claim 1, for use in medicine.

6. The method of claim 3, wherein the compound according to claim 1 performs as an imaging or diagnostic agent.

7. The method of claim 6, wherein the compound is isotopically labelled.

* * * * *